US006171588B1

(12) United States Patent
Carron et al.

(10) Patent No.: US 6,171,588 B1
(45) Date of Patent: Jan. 9, 2001

(54) ANTI-$\alpha_V\beta_3$ INTEGRIN ANTIBODY ANTAGONISTS

(75) Inventors: Christopher P. Carron, Wildwood; Debra M. Meyer; George A. Nickols, both of Wentzville, all of MO (US)

(73) Assignee: G. D. Searle & Company, Skokie, IL (US)

( * ) Notice: Under 35 U.S.C. 154(b), the term of this patent shall be extended for 0 days.

(21) Appl. No.: 09/057,486

(22) Filed: Apr. 9, 1998

Related U.S. Application Data

(60) Provisional application No. 60/043,853, filed on Apr. 11, 1997.

(51) Int. Cl.$^7$ ............... A61K 39/395; C07K 16/28; C07K 16/18; C12N 5/12

(52) U.S. Cl. ............... 424/143.1; 424/130.1; 424/141.1; 424/143.1; 424/152.1; 424/172.1; 435/70.21; 435/326; 435/332; 435/334; 435/346; 530/387.1; 530/388.1; 530/388.2; 530/388.22

(58) Field of Search ............... 424/130.1, 141.1, 424/172.1; 435/70.21, 334; 530/387.1, 388.2

(56) References Cited

U.S. PATENT DOCUMENTS

| | | |
|---|---|---|
| 4,659,839 | 4/1987 | Nicolotti et al. . |
| 4,816,567 | 3/1989 | Cabilly et al. . |
| 5,057,604 | 10/1991 | Brown . |
| 5,130,118 | 7/1992 | Johnson et al. . |
| 5,149,780 | 9/1992 | Plow et al. . |
| 5,252,748 | 10/1993 | Yamauchi et al. . |
| 5,306,620 | 4/1994 | Ginsberg et al. . |
| 5,591,829 | 1/1997 | Matsushita . |
| 5,631,236 | 5/1997 | Woo et al. . |
| 5,652,109 | * 7/1997 | Kim et al. . |
| 5,679,318 | 10/1997 | Vanderheyden et al. . |
| 5,681,927 | 10/1997 | Fritzberg et al. . |
| 5,693,761 | 12/1997 | Queen et al. . |
| 5,753,230 | * 5/1998 | Brooks et al. . |

FOREIGN PATENT DOCUMENTS

| | | |
|---|---|---|
| 0 653 439 | 5/1995 | (EP) . |
| WO 89/05155 | 6/1989 | (WO) . |
| WO 90/07936 | 7/1990 | (WO) . |
| WO 93/20229 | 10/1993 | (WO) . |
| WO 95/25543 | 9/1995 | (WO) . |

OTHER PUBLICATIONS

Carron et al. Cancer Research 58:1930–1935 (1998).*
A. Nichols, et al., "Antiangiogenic and anticancer activities of the antagonists of integrin $\alpha_v\beta_3$", Proc. Am. Assoc. Cancer Res., vol. 38, No. A1389 pp. 206, (Mar., 1997).
E. Aboud–Pirak, et al., "Inhibition of Human Tumor Growth in Nude Mice by a Conjugate of Doxorubicin With Monoclonal Antibodies to Epidermal Growth Factor Receptor", Proc. Natl. Acad. Science, vol. 86, pp. 3778–3781, (1989).

A. Adamis, et al., "Increased Vascular Endothelial Growth Factor Levels in the Vitreous of Eyes With Proliferative Diabetic Retinopathy", Amer. Journal of Ophthalmology vol. 118, pp. 445–450, (1994).
L. Apelgren, et al., "Antitumor Activity of the Monoclonal Antibody–Vinca Alkaloid Immuconjgate LY203725 (KS1/4–4–Desacetylvinblastine–3–carboxhydrazide) in a Nude Mouse Model of Human Ovarian Cancer", Cancer Research, vol. 50, 3540–3544, (1990).
A. Bachmann et al., "Integrin receptor–targeted transfer peptides for efficient delivery of antisense oligodeoxynucleotides", Journal of Molecular Medicine, vol. 76, No. 2, pp. 126–132 (1998).
J. Bennett, et al., "Inhibition of fibrinogen binding to stimulated human platelets by a monoclonal antibody", Proc. Natl. Acad. Science, vol. 80, pp. 2417–2421, (1983).
S. Bodary et al., "The Integrin $\beta 1$ Submit Associates with the Vitronectin Receptor $\alpha v$ Subunit to Form a Novel Vitronectin Receptor in a Human Embryonic Kidney Cell Line", J. Biolog. Chem., vol. 265, pp. 5938–5941, (1990).
P. Brooks, et al., "Antiintegrin $\alpha_v\beta_3$ blocks human breast cancer growth and angiogenesis in human skin", J. Clin. Invest., vol. 96, pp. 1815–1822, (1995).
P. Brooks, et al., "Integrin $\alpha_v\beta_3$ Antagonists Promote Tumor Regression by Inducing Apoptosis of Angiogenic Blood Vessels", Cell Press, vol. 79, pp. 1157–1164, (1994).
P. Brooks, et al., "Requirement of Vascular Integrin $\alpha_v\beta_3$ for Angioenesis", Science, vol. 264, (1994).
D. Cheresh, "Human endothelial cells synthesize and express an Arg–Gly–Asp–directed adhesion receptor involved in attachment to fibrinogen and von Willebrand factor", Proceedings of the National Academy of Sciences, vol. 84, No. 18, pp. 6471–6475, (1987).
E. Choi, et al., "Inhibition of neointimal hyperplasia by blocking $\alpha_v\beta_3$ integrin with a small peptide antagonist Gpen GRGDSPCA", J. of Vascular Surgery, vol. 19, No. 1, pp. 125–134, (1994).
A. Chuntharapai, et al., "Blocking Monoclonal Antibodies to $\alpha V\beta_3$ Integrin Ia Present on Human Osteoclasts",Cell Research, vol. 205, No. 2, (1993).
S. Crooke, "Therapeutic Applications of Oligonucleotides", Bio/Technology, vol. 10, pp. 882–886, (1992).
R. Dillman, et al., "Superiority of an Acid–labile Daunorubican–Monoclonal Antibody Immunoconjugate Compared to Free Drug", Cancer Research, vol. 48, pp. 6097–6102, (1998).

(List continued on next page.)

Primary Examiner—Philip Gambel
(74) Attorney, Agent, or Firm—Fitzpatrick, Cella, Harper & Scinto

(57) ABSTRACT

Monoclonal antibodies that recognize the $\alpha_v$ $\beta_3$ integrin receptor complex, but do not significantly bind to $\alpha_{IIb}\beta_{IIIa}$, inhibit $\alpha_v\beta_3$ integrin-mediated diseases.

33 Claims, 5 Drawing Sheets

(1 of 5 Drawing Sheet(s) Filed in Color)

OTHER PUBLICATIONS

M. Doerr, et al., "The Roles of Integrins and Extracellular Matrix Proteins in the Insulin–like Growth I–stimulated Chemotaxis of Human Breast Cancer Cells", J. Biological Chemistry, vol. 271, No. 5, pp. 2443–2447, (1996).

J. Fisher, et al., "Inhibition of Osteoclastic Bone Resorption in Vivo by Eshistatin, an Arginyl–Glycyl–Aspartyl (RGD)–Containing Protein", Endocrinology, vol. 132, pp. 1411–1413, (1983).

G. Fuller et al., "Fibrinogen", Methods in Enzymol, vol. 163, pp. 474–485, (1988).

G. Galfre et al., "Immunochemical Techniques, Methods in Enzymology", vol. 73, pp. 3–46, (1981).

M. Ginsberg, et al., "Reduced Surface Expression and Binding of Fibronectin by Thrombin–stimulated Thrombasthenic Platelets", J. Clin Invest, vol. 71, pp. 619–624, (1983).

J. Goding, "Antibody Procuction by Hybridomas", Journal of Immunological Methods, vol. 39, pp. 285–308, (1980).

G. Gui et al., "In vitro regulation of human breast cancer cell adhesion and invasion via integrin receptors to the extracellular matrix", British Journal of Surgery, vol. 82, pp. 1192–1196, (1995).

M. Humphries, et al., "Investigation of the Biological Effects of Anti–Cell Adhesive Synthetic Peptides That Inhibit Experimental Metastasis of B16–F10 Murine Melanoma Cells", J. Clin Invest., vol. 81, pp. 782–790, (1988).

E. Hurwitz, et al., "The Covalent Binding of Daunomycin and Adriamycin to Antibodies, with Retention of Both Drug and Antibody Activities", Cancer Research, vol. 35, pp. 1175–1181, (1975).

E. Hurwitz, et al., "The Covalent Linking of Two Nucleotide Analogues to Antibodies", Journal of Med. Chem., vol. 28, pp. 137–140, (1985).

E. Hurwitz, et al., "Daunomycin–Immunoglobulin Conjugates, Uptake and Activity In Vitro", Eur. J. Cancer vol. 14, pp. 1213–1220, (1978).

E. Hurwitz, et al., "Soluble Macromolecules as Carriers for Daunorubicin", Journal of Applied Biochemistry, vol. 2, pp. 25–35, (1980).

W. Huse, et al., "Generation of a Large Combinatorial Library of the Immunoglobulin Repertoire in Phage Lambda", Science, vol. 246, pp. 1275–1281, (1989).

D. Johnson, et al., "in vivo antitumor activity demonstrated with squamous carcinoma reactive monoclonal antibody–Vinca immunoconjugates", Cancer Immunol Immunother, vol. 27, pp. 241–245, (1988).

I. Kimura, et al., "Production of Tumor Antibody–Neocarzinostatin(NCS) Conjugate and its Biological Activities", Cancer Immunology and Immunotherapy, vol. 7, pp. 235–242, (1980).

G. Kohler and C. Milstein, "Continuous cultures of fused cells secreting antibody of predefined specificity", Nature vol. 256, pp. 495–497, (1975).

P. Kulkarni, et al., "Covalent Binding of Methotrexate to Immunoglobulins and the Effect of Antibody–linked Drug on Tumor Growth in Vivo", Cancer Research, vol. 41, pp. 2700–2706, (1981).

E. Lavie, et al., "Monoclonal antibody L6–daunomycin conjugates constructed to release free drug at the lower pH of tumor tissue", Cancer Immunology Immunotherapy, pp. 223–230, (1991).

M. Lehmann, et al., "A Monoclonal Antibody Inhibits Adhesion to Fibronectin and Vitronectin of a Colon Carcinoma Cell Line and Recognizeds the Integrins $\alpha_v\beta_3$, $\alpha_v\beta_5$ and $\alpha_v\beta_6^1$", Cancer Research, vol. 54, pp. 2102–2107, (1994).

Y. Manabe, et al., "Production of a Monoclonal Antibody–Bleomycin Conjugate Utilizing Dextran T–40 and the Antigen–Targeting Cytotoxicity of the Conjugate", Biochemical and Biophysical Research Communications, vol. 115, No. 3, pp. 1009–1014, (1983).

D. McIntosh, et al., "Pharmacokinetics and Tissue Distribution of Cisplatin and Conjugates of Cisplatin With Carboxymethyldextran and A5B7 Monoclonal Antibody in CD1 Mice", Journ. Of Pharmaceutical Sciences, vol. 86, No. 12, pp. 1478–1483, (1997).

A. Montgomery, et al., "Integrin $\alpha_v\beta_3$ rescues melanoma cells from apoptosis in three–dimensional dermal collagen", Proceedings of the National Academy of Science, vol. 91, pp. 8856–8860, (1994).

S. Morrison, et al., "Chimeric Human Antibody Molecules: Mouse antigen–binding Domains With Humans Constant Region Domains", Proceeding of the National Academy of Sciences, vol. 81, pp. 6851–6855, (1984).

B. Mueller, et al., "Antibody Conjugates with Morpholinodoxorubicin and Acid–Cleavable Linkers", Bioconjugate Chem., vol. 1, pp. 325–330, (1990).

M. Naramura, et al., "Mechanisms of cellular cytotoxicity mediated by a recombinant antibody–IL2 fusion protein against human melanoma cells", Immunology Letters, vol. 39, pp. 91–99, (1994).

H. Niman, et al., "Generation of protein–reactive antibodies by short peptides is an event of high frequency", Proc. Natl. Acad. Science, vol. 80, pp. 4949–4953, (1983).

K. Ondrick, et al., "Angiogenesis", Clinics in Pediatric Medicine and Surgery, vol. 9, No. 1, pp. 186–200, (1992).

M. Page, et al., "Dawnomycin Targeting To Human Colon Carcinoma Cells Using Drug–Anticea Conjugates", Proc. Am. Assoc. Cancer Res., vol. 22, p. 211, (1981).

M. Page, et al., "Drug Targeting With Monoclonal Antibodies", C.10 Drug Targeting, pp. 933–936 (1981.

D. Peacock, et al., "Angiogenesis Inhibition Suppresses Collagen Arthritis", J. Exp. Med. pp. 1135–1138, (1992).

G. Pietersz, et al., "Immunochemotherapy of a Murine Thymoma with the Use of Idarubicin Monoclonal Antibody Conjugates", Cancer Research, vol. 48, pp. 926–931, (1988).

J. Price, et al., "The Use of a Genotypic Marker to Demonstrate Clonal Dominance During the Growth and Metastasis of a Human Breast Carcinoma in Nude Mice", Int. J. Cancer, pp. 968–971, (1990).

R. Pytela et al., "Arginine–Glycine–Aspartic Acid Adhesion Receptors", Methods in Enzymol., vol. 144, pp. 475–489, (1987).

R. Reisfeld, et al., "Recombinant Antibody Fusion Proteins for Cancer Immunotherapy", Current Topics in Microbiology 213/III and Immunology, pp. 28–53 (1996).

S. Rybak, et al., "Humanization of immunotoxins", Proc. Natl. Acad. Science, vol. 89, pp. 3165–3169, (1992).

Z. Ruggeri, et al., "Glanzamann thrombasthenia: Deficient binding of von Willebrand factor to thrombin–stimulated platelets", Proceedings of the National Academy of Sciences, vol. 79, pp. 6038–6041 (1982).

L. Sastry, et al., "Cloning of the immunological repertoire in Escherichia coli for generation of monoclonal catalytic antibodies: Construction of a heavy chain variable region–specific c DNA library", Proceedings of the National Academy of Sciences, vol. 86, pp. 5728–5732, (1989).

M. Sato, et al., "Echistatin Is a Potent Inhibitor of Bone Resorption in Culture", The Journal of Cell Biology, vol. 111, pp. 1713–1722, (1990).

R. Seftor, et al., "Role of the $\alpha v \beta 3$ integrin in human melanoma cell invasion", Proc. Natl. Acad. Science, pp. 1557–1561, (1992).

C. Seigall, et al., "A Single–Chain Immuotoxin Fusion Protein that Cures Human Breast Carcinoma Xenografts in Athymic Mice and Rats", In Vitro and In Vivo Characterization of BR96 sFv–PE40 (1994).

M. Smyth, et al., "Selective Enhancement of Antitumor Activity of N–Acetyl Melphalan upon Conjugation to Monoclonal Antibodies", Cancer Research, vol. 47, pp. 62–69, (1987).

J. Starling, et al., "In Vivo Antitumor Activity of a Monoclonal Antibody–Vinca Alkaloid Immunoconjugate Directed against a Solid Tumor Membrane Antigen Characterized by Heterogeneous Expression and Noninternalization of Antibody–Antigen Complexes", Cancer Research, vol. 52, pp. 2965–2972, (1991).

T. Suzuki, et al., "The Preparation of Mitomycin C, Adriamycin and Daunomycin Covalently Bound to Antibodies as Improved Cancer Chemotherapeutic Agents", Chem. Pharm. Bull, vol. 29, pp. 844–848, (1981).

P. Trail, et al., "Antigen–specific Activity of Carcinoma–reactive BR64–Doxorubicin Conjugates Evaluated in Vitro and in Human Tumor Xenograft Models",Cancer Research, vol. 52, pp. 5693–5700, (1992).

P. Trail, et al., "Cure of Xenografted Human Carcinomas by BR96–Doxorubicin Immunoconjugates", Science, vol. 261, pp. 212–215, (1993).

Y. Tsukada et al., "An Anti–$\alpha$–Fetoprotein Antibody–Daunorubicin Conjugate With a Novel Poly–L–glutamic Acid Derivative as Intermediate Drug Carrier", J. Natl. Cancer Inst., vol. 73, pp. 721–729, (1984).

E. Uhlmann, "Antisense Oligonucleotides: A New Therapeutic Principle", Chemical Reviews, vol. 90, No. 4, pp. 543–584, (1990).

M. Wagner, et al., "Nucleotide sequence of the thymidine kinase gene of herpes simplex virus type 1",Proceeding of the National Academy of Sciences, vol. 78, No. 3, pp. 1441–1445, (1981).

N. Weidner, "Tumor Angiogenesis: Review of Current Applications in Tumor Prognostication", Seminars in Diagnostic Pathology, vol. 10, No. 4, Nov. pp. 302–313, (1993).

J. White, "Integrins as virus receptors", Current Biology, vol. 3, No. 9, pp. 596–599, (1993).

S. Wong, "Preparation of Immunotoxins and Other Drug Conjugates For Targeting Theraputics", Chemistry of Protein Conjugation, CRC Handbook Chapter 11, pp. 267–293, (1991).

T. Yatohgo, et al., "Novel Purification of Vitronectin from Human Plasma by heparin Affinity Chromatography", Cell Structure and Function, vol. 13, pp. 281–292, (1988).

* cited by examiner

SEQUENCE LISTING

```
<160> NUMBER OF SEQ ID NOS: 3

<210> SEQ ID NO 1
<211> LENGTH: 55
<212> TYPE: PRT
<213> ORGANISM: Artificial Sequence
<220> FEATURE:
<223> OTHER INFORMATION: Description of Artificial Sequence:Nucleocapsid
      protein 7 of HIV-1
<220> FEATURE:
<221> NAME/KEY: ZN_FING
<222> LOCATION: (15)..(28)
<220> FEATURE:
<221> NAME/KEY: ZN_FING
<222> LOCATION: (36)..(49)
<300> PUBLICATION INFORMATION:
<303> JOURNAL: J. Mol. Med.
<304> VOLUME: 76
<306> PAGES: 126-132
<307> DATE: 1998

<400> SEQUENCE: 1
```

Met Gln Arg Gly Asn Phe Arg Asn Gln Arg Lys Met Val Lys Cys Phe
 1               5                  10                  15

Asn Cys Gly Lys Glu Gly His Thr Ala Arg Asn Cys Arg Ala Pro Arg
            20                  25                  30

Lys Lys Gly Cys Trp Lys Cys Gly Lys Glu Gly His Gln Met Lys Asp
        35                  40                  45

Cys Thr Glu Arg Gln Ala Asn
    50                  55

```
<210> SEQ ID NO 2
<211> LENGTH: 35
<212> TYPE: PRT
<213> ORGANISM: Artificial Sequence
<220> FEATURE:
<223> OTHER INFORMATION: Description of Artificial Sequence:Nucleocapsid
      protein 7 of HIV-1  fragment
<220> FEATURE:
<221> NAME/KEY: ZN_FING
<222> LOCATION: (15)..(28)
<300> PUBLICATION INFORMATION:
<303> JOURNAL: J. Mol. Med.
<304> VOLUME: 76
<306> PAGES: 126-132
<307> DATE: 1998

<400> SEQUENCE: 2

Met Gln Arg Gly Asn Phe Arg Asn Gln Arg Lys Met Val Lys Cys Phe
  1               5                  10                  15

Asn Cys Gly Lys Glu Gly His Thr Ala Arg Asn Cys Arg Ala Pro Arg
             20                  25                  30

Lys Lys Gly
         35

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence:c-myb
      antisense oligonucleotide
<300> PUBLICATION INFORMATION:
<303> JOURNAL: J. Mol. Med.
<304> VOLUME: 76
<306> PAGES: 126-132
<307> DATE: 1998

<400> SEQUENCE: 3
gtgccggggt cttcgggc                                                 18
```

US 6,171,588 B1

ANTI-$\alpha_v\beta_3$ INTEGRIN ANTIBODY ANTAGONISTS

This application claims the benefit of U.S. Provisional patent application No. 60/043,853, filed Apr. 11, 1997.

BACKGROUND OF THE INVENTION

Field of the Invention

The present invention relates to antibodies which are useful as $\alpha_v\beta_3$ integrin antagonists and as such are useful in pharmaceutical compositions and in methods for treating conditions mediated by $\alpha_v\beta_3$ by inhibiting or antagonizing $\alpha_v\beta_3$ integrins.

BACKGROUND OF THE INVENTION

Integrins are a group of cell surface glycoproteins that mediate cell adhesion and therefore are mediators of cell adhesion interactions that occur in various biological processes. Integrins are heterodimers composed of noncovalently linked $\alpha$ and $\beta$ polypeptide subunits. Currently at least eleven different $\alpha$ subunits have been identified and at least six different $\beta$ subunits have been identified. The various $\alpha$ subunits can combine with various $\beta$ subunits to form distinct integrins.

The integrin identified as $\alpha_v\beta_3$ (also known as the vitronectin receptor) has been identified as an integrin that plays a role in various conditions or disease states including tumor metastasis, solid tumor growth (neoplasia), osteoporosis, Paget's disease, humoral hypercalcemia of malignancy, angiogenesis, including tumor angiogenesis, retinopathy, arthritis, including rheumatoid arthritis, periodontal disease, psoriasis and smooth muscle cell migration (e.g. restenosis). Additionally, it has been found that such integrin inhibiting agents would be useful as antivirals, antifungals and antimicrobials. Thus, antibodies that selectively inhibit or antagonize $\alpha_v$ $\beta_3$ would be beneficial for treating such conditions.

It has been shown that the $\alpha_v\beta_3$ integrin binds to a number of Arg-Gly-Asp (RGD) containing matrix macromolecules, such as fibrinogen (Bennett et al., *Proc. Natl. Acad. Sci. USA*, Vol. 80 (1983) 2417), fibronectin (Ginsberg et al., *J. Clin. Invest.*, Vol. 71 (1983) 619–624), and von Willebrand factor (Ruggeri et al., *Proc. Natl. Acad. Sci. USA*, Vol. 79 (1982) 6038). Compounds containing the RGD sequence mimic extracellular matrix ligands so as to bind to cell surface receptors. However, it is also known that RGD peptides in general are non-selective for RGD dependent integrins. For example, most RGD peptides that bind to $\alpha_v\beta_3$ also bind to $\alpha_v\beta_5$, $\alpha_v\beta_1$, and $\alpha_{IIb}\beta_{IIIa}$. Antagonism of platelet $\alpha_{IIb}\beta_{IIIa}$ (also known as the fibrinogen receptor) is known to block platelet aggregation in humans. In order to avoid bleeding side-effects when treating the conditions of disease states associated with the integrin $\alpha_v\beta_3$, it would be beneficial to develop selective antagonists of $\alpha_v\beta_3$ as opposed to $\alpha_{IIb}\beta_{IIIa}$. Antibodies selective for $\alpha_v\beta_3$ offer such an advantage.

SUMMARY OF THE INVENTION

The present invention involves murine monoclonal antibodies produced by hybridomas generated from mice immunized with human integrin $\alpha_v\beta_3$, or cells expressing $\alpha_v\beta_3$, that block the functional activity of $\alpha_v\beta_3$. More specifically, the present invention involves murine monoclonal antibodies, P113-7D6, P112-4C1, P113-12A6, P112-llD2, P112-10D4 and P113-lF3, which are complex-specific for $\alpha_v\beta_3$ in the sense that they immunoreact with an integrin $\alpha_v\beta_3$ complex and do not react with either of the integrin $\alpha_v$ or $\beta_3$ subunits individually. In addition, the inventive monoclonal antibodies do not significantly bind to $\alpha_{IIb}\beta_{IIIa}$, or other RGD recognizing integrins. The monoclonal antibodies of this invention may also be used in a method of treating $\alpha_v\beta_3$ integrin-mediated diseases or conditions by administering to a mammal in need of treatment an effective amount of an $\alpha_v\beta_3$ integrin antibody that acts as an $\alpha_v\beta_3$ integrin antagonist or inhibitor.

The monoclonal antibodies of the present invention can also be used in methods for delivering either cytotoxic or cytostatic compounds, nucleic and deoxynucleic acids or radioisotopes to cells having $\alpha_v\beta_3$-integrin. For example, the monoclonal antibodies of the present invention (or a Fab, Fab', F(ab')2 and F(v) fragments thereof containing a paratope for $\alpha_v\beta_3$-integrin) can be conjugated to the cytotoxic or cytostatic compounds, nucleic acids or radioisotopes and then contacted with tissue or cells in vivo or in vitro.

BRIEF DESCRIPTION OF THE DRAWINGS

The file of this patent contains one photograph executed in color. Copies of this patent with the color photograph will be provided by the Patent and Trademark Office upon request and payment of the necessary fee.

DETAILED DESCRIPTION OF THE INVENTION

Metastases

Figure 1A:
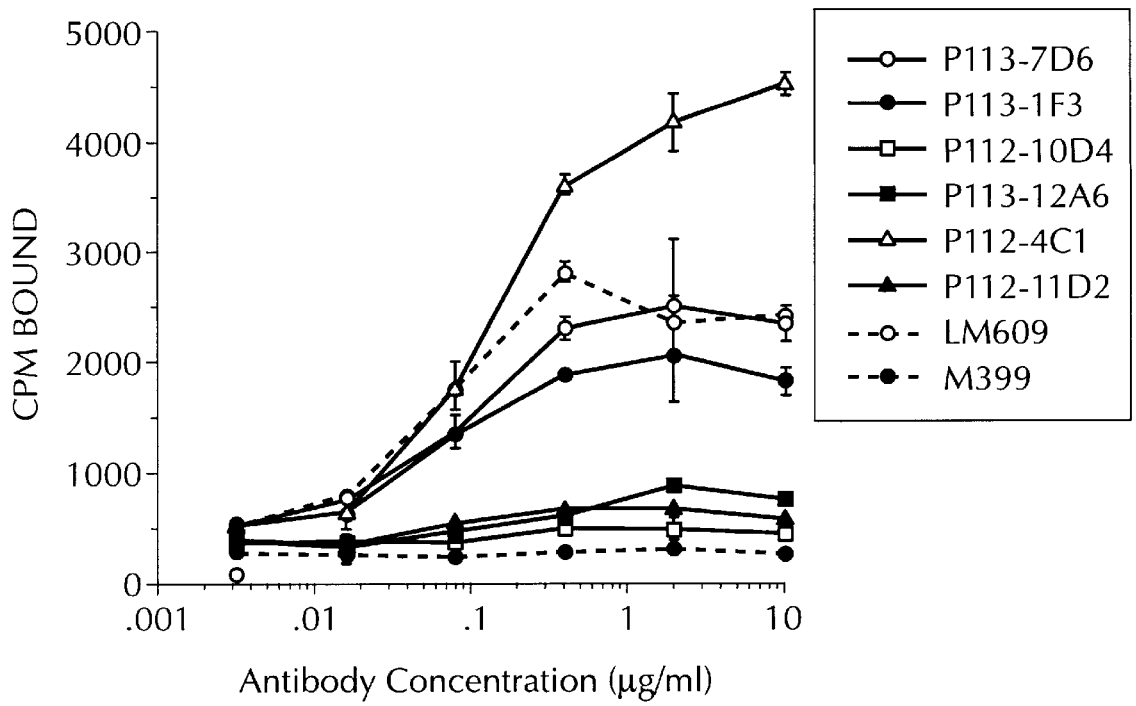
FIG. 1 shows that the purified anti-$\alpha_v\beta_3$ monoclonal antibodies P113-7D6, P112-4C1, P113-12A6, P112-llD2, P112-10D4, P113-1F3, LM609 (obtained from Chemicon) binds $^{125}$I-labeled $\alpha_v\beta_3$ (panel A) but not $^{125}$I-labeled $\alpha_{IIb}\beta_{IIIa}$ (panel B). The control monoclonal antibody, M399, binds neither $^{125}$I-labeled $\alpha_v\beta_3$ nor $\alpha_{IIb}\beta_{IIIa}$. M399 is an irrelevant isotype matched control antibody produced by Monsanto Company. LM609 antibody was purchased from Chemicon (Tamecula, Calif.).

Integrins are believed to be involved in, amongst other biological processes, tumor metastasis. Studies have shown, (Humphries, et al., *J. Clin. Invest., Vol.* 81 (1988) 782), that RGD-like compounds can interfere with experimental metastasis wherein tumor cells are injected directly into the blood.

Tumor cell invasion occurs by a three step process:
1) tumor cell attachment to extracellular matrix;
2) proteolytic dissolution of the matrix; and
3) movement of the cells through the dissolved barrier.
This process can occur repeatedly and can result in metastases at sites distant from the original tumor.

Seftor et al. (*Proc Natl. Acad. Sci. USA,* Vol. 89 (1992) 1557) have shown that the $\alpha_v\beta_3$ integrin has a biological function in melanoma cell invasion. Montgomery et al., (*Proc. Natl. Acad. Sci. USA,* Vol. 91 (1994) 8856) have demonstrated that the integrin $\alpha_v\beta_3$ expressed on human melanoma cells promotes a survival signal, protecting the cells from apoptosis. Accordingly, mediation of the tumor cell metastatic pathway by interference with the $\alpha_v\beta_3$ integrin cell adhesion receptor to impede tumor metastasis would be beneficial.

Brooks et al. (*Cell,* Vol. 79 (1994) 1157) have demonstrated that antagonists of $\alpha_v\beta_3$ provide a therapeutic approach for the treatment of neoplasia (inhibition of solid tumor growth) since systemic administration of $\alpha_v\beta_3$ antagonists causes dramatic regression of various histologically distinct human tumors.

The monoclonal antibodies of the present invention may also be used in a method of treating $\alpha_v\beta_3$ integrin-mediated diseases, such as tumor metastasis by administering to a mammal in need of treatment an effective amount of an $\alpha_v\beta_3$ integrin antibody that acts as an $\alpha_v\beta_3$ integrin antagonist or inhibitor. Reference is made to co-pending U.S. application Ser. No. 09/057,490), contemporaneously filed herewith in the names of Christopher P. Carron, Debra M. Meyer, G. Allan Nickols and Jeffrey W. Smith and entitled Methods For Using Anti-$\alpha_v\beta_3$ Integrin Antibody Antagonists, the disclosure of which is incorporated by reference herein.

Tumor Growth/Angiogenesis

The adhesion receptor integrin $\alpha_v\beta_3$ was identified as a marker of angiogenic blood vessels in chick and man and plays a critical role in angiogenesis or neovascularization (Brooks et al., *J-Clin-Invest,* Vol. 96 (1995) 1815). Angiogenesis is characterized by the invasion, migration and proliferation of smooth muscle and endothelial cells. Antagonists of $\alpha_v\beta_3$ inhibit this process by selectively promoting apoptosis of cells in neovasculature. The growth of new blood vessels, or angiogenesis, also contributes to pathological conditions such as diabetic retinopathy (Adonis et al., *Amer. J. Ophthal.,* Vol. 118, (1994) 445), rheumatoid arthritis (Peacock et al., *J. Exp. Med., Vol.* 175, (1992) 1135) and osteoarthritis (Ondrick et al., *Clin.-Podiatr.-Med.-Surg.,* Vol. 9, (1992) 185). Therefore, $\alpha_v\beta_3$ antagonists would be useful therapeutic targets for treating such conditions associated with neovascularization (Brooks et al., *Science,* Vol. 264, (1994) 569). Because angiogenesis occurs normally in the female reproductive organs, antagonists of $\alpha_v\beta_3$ would be useful in controlling fertility.

Osteoporosis

It has been reported that the cell surface receptor $\alpha_v\beta_3$ is the major integrin on osteoclasts responsible for attachment to bone. Osteoclasts cause bone resorption and when such bone resorbing activity exceeds bone forming activity it results in osteoporosis (a loss of bone), which leads to an increased number of bone fractures, incapacitation and increased mortality. Antagonists of $\alpha_v\beta_3$ have been shown to be potent inhibitors of osteoclastic activity both in vitro (Sato et al., *J. Cell. Biol., Vol.* 111 (1990) 1713) and in vivo (Fisher et al., *Endocrinology,* Vol. 132 (1993) 1411. Antagonism of $\alpha_v\beta_3$ leads to decreased bone resorption and therefore restores a normal balance of bone forming and resorbing activity. Thus it would be beneficial to provide antagonists of osteoclast $\alpha_v\beta_3$ which are effective inhibitors of bone resorption and therefore are useful in the treatment or prevention of osteoporosis.

Restenosis

The role of the $\alpha_v\beta_3$ integrin in smooth muscle cell migration also makes it a therapeutic target for prevention or inhibition of neointimal hyperplasia which is a leading cause of restenosis after vascular procedures (Choi et al., *J. Vasc. Surg. Vol.* 19(1) (1994) 125). Prevention or inhibition of neointimal hyperplasia by pharmaceutical agents to prevent or inhibit restenosis would be beneficial.

Viral Infection

White (*Current Biology,* Vol. 3(9) (1993) 596) has reported that adenovirus uses $\alpha_v\beta_3$ for entering host cells. The integrin appears to be required for endocytosis of the virus particle and may be required for penetration of the viral genome into the host cell. Thus antibodies which inhibit $\alpha_v\beta_3$ would find usefulness as antiviral agents.

Anti-Integrin Antibodies

A number of anti-integrin antibodies are known. Doerr et al. (*J.B.C.,* Vol. 271 (1996) 2443) reported that a blocking antibody to $\alpha_v\beta_5$ integrin in vitro inhibits the migration of MCF-7 human breast cancer cells in response to stimulation from IGF-1. Gui et al. (*British J. Surgery,* Vol. 82 (1995) 1192) report that antibodies against $\alpha_v\beta_5$ and $\beta_1$ and $\beta_5$ inhibit in vitro chemoinvasion by human breast cancer carcinoma cell lines Hs578T and MDA-MB-231. Lehman et al. (*Cancer Research,* Vol. 54 (1994) 2102) show that a monoclonal antibody (69-6-5) reacts with several $\alpha_v$ integrins including $\alpha_v\beta_3$ and inhibited colon carcinoma cell adhesion to a number of substrates, including vitronectin. Brooks et al. (*Science,* Vol. 264 (1994) 569) show that blockade of integrin activity with an anti-$\alpha_v\beta_3$ monoclonal antibody inhibits tumor-induced angiogenesis of chick chorioallantoic membranes by human M21-L melanoma fragments. Chuntharapai et al. (*Exp. Cell. Res.,* Vol. 205 (1993) 345) discloses monoclonal antibodies 9G2.1.3 and IOC4.1.3 which recognize the $\alpha_v\beta_3$ complex, the latter monoclonal antibody is said to bind weakly or not at all to tissues expressing $\alpha_v\beta_3$ with the exception of osteoclasts and was suggested to be useful for in vivo therapy of bone disease. The former monoclonal antibody is suggested to have potential as a therapeutic agent in some cancers.

Ginsberg et al., U.S. Pat. No. 5,306,620 discloses antibodies that react with integrin so that the binding affinity of integrin for ligands is increased. As such these monoclonal antibodies are said to be useful for preventing metastasis by immobilizing melanoma tumors. Brown, U.S. Pat. No. 5,057,604 discloses the use of monoclonal antibodies to $\alpha_v\beta_3$ integrins that inhibit RGD-mediated phagocytosis enhancement by binding to a receptor that recognizes RGD sequence containing proteins. Plow et al., U.S. Pat. No. 5,149,780 discloses a protein homologous to the RGD epitope of integrin β subunits and a monoclonal antibody that inhibits integrin-ligand binding by binding to the $\beta_3$ subunit. That action is said to be of use in therapies for adhesion-initiated human responses such as coagulation and some inflammatory responses.

As a result of the present invention, monoclonal antibodies can be used in a method for blocking $\alpha_v\beta_3$-mediated events such as cell adhesion, osteoclast-mediated bone resorption, restenosis, ocular neovascularization and growth of hemangiomas, as well as neoplastic cell or tumor growth and dissemination. The inventive monoclonal antibodies can also be used for antibody-mediated targeting and delivery of therapeutics for disrupting or killing $\alpha_v\beta_3$ bearing neoplasms and tumor-related vascular beds. In addition, the inventive monoclonal antibodies can be used for visualization or imaging of $\alpha_v\beta_3$ bearing neoplasms or tumor related vascular beds, for example, by NMR or immunoscintigraphy.

In addition, these monoclonal antibodies detect $\alpha_v\beta_3$ in solution and in frozen tissue sections and on the surface of cells and therefore these monoclonal antibodies may be used for the detection and characterization of $\alpha_v\beta_3$-bearing tumor and endothelial cells in human malignancies. Accordingly, the monoclonal antibodies of the present invention may be used for immunochemical and immunohistochemical identification of tumor vasculature. Since the integrin $\alpha_v\beta_3$ is minimally expressed on resting or normal blood vessels, but is significantly up-regulated on vascular cells within human tumors (Brooks et al., *Cell,* Vol. 79 (1994) 1157; Brooks et al., *Science,* Vol. 264 (1994) 569; Brooks, et al., *J-Clin-Invest,* Vol. 96 (1995) 1815), $\alpha_v\beta_3$ may be considered a marker of human tumor-associated blood vessels and tumor growth (Brooks, et al., *J-Clin-Invest,* Vol. 96 (1995) 1815). Consequently, antibodies that recognize $\alpha_v\beta_3$ may be used as an immunodiagnostic agent to identify tumor-related blood vessels or vascular beds using conventional immunohistochemical techniques. Further, since the integrin $\alpha_v\beta_3$ is a marker of tumor-associated blood vessels and recent findings indicate that blood vessel density is a prognostic indicator of cancer and disease status (Weidner, *Semin-Diagn-Pathol,* Vol. 10 (1993) 302) antibody that recognize $\alpha_v\beta_3$ may be used as a component of a diagnostic device or technique to measure tumor-related blood vessel abundance or density and to define disease prognosis. Specifically, histologic sections from fresh-frozen or formalin-fixed paraffin embedded tumor tissue are immunostained with $\alpha_v\beta_3$ antibody, preferably using the $\alpha_v\beta_3$ antibody at concentration of 0.1–50 μg/ml, using techniques and procedures known to those skilled in the art. $\alpha_v\beta_3$ antibody bound to vascular endothelial cells in the tissue can be visualized using a secondary agent, usually a second antibody, that permits localization of the $\alpha_v\beta_3$ antibody binding within the tissue section. Preferably the second antibody reacts or binds with the $\alpha_v\beta_3$ antibody and has an attached reporter molecule, e.g., an anti-mouse antibody with an attached enzyme or fluorescent marker. The number and area of immunostained blood vessels in the tissue can then be counted by microscopic techniques, familiar to those skilled in the art, to assess tumor blood vessel density or abundance.

The monoclonal antibodies of the present invention can also be used in methods for delivering either cytotoxic or cytostatic compounds, nucleic and deoxynucleic acids or radioisotopes to cells having $\alpha_v\beta_3$-integrin. For example, the monoclonal antibodies of the present invention (or a Fab, Fab', F(ab')2 and F(v) fragments thereof containing a paratope for $\alpha_v\beta_3$-integrin) can be conjugated to the cytotoxic or cytostatic compounds, nucleic acids or radioisotopes and then contacted with tissue or cells in vivo or in vitro.

Antibodies and Antibody Compositions

The term "antibody" refers to immunoglobulin molecules and immunologically active portions of immunoglobulin molecules, i.e., molecules that contain an antibody combining site or paratope. Illustrative antibody molecules are intact immunoglobulin molecules, substantially intact immunoglobulin molecules and those portions of an immunoglobulin molecule that contain the paratope, including those portions known in the art as Fab, Fab', F(ab')2 and F(v).

The term "antibody combining site" refers to that structural portion of an antibody molecule comprised of a heavy and light chain variable and hypervariable regions that specifically binds (immunoreacts with) antigen. The term "immunoreact" refers to binding between an antigenic determinant-containing molecule and a molecule containing an antibody combining site such as a whole antibody molecule or a portion thereof. The term "antigenic determinant" refers to the actual structural portion of the antigen that is immunologically bound by an antibody combining site. The term is also used interchangeably with "epitope".

As used herein, the term "specifically binds" refers to a non-random binding reaction between two molecules, for example between an antibody molecule immunoreacting with an antigen or between a cell surface integrin receptor and a ligand molecule. Illustrative of a specifically-bound receptor-ligand complex is that between platelet $\alpha_{IIb}\beta_{IIIa}$ and fibrinogen at the platelet surface.

Figure 1B:
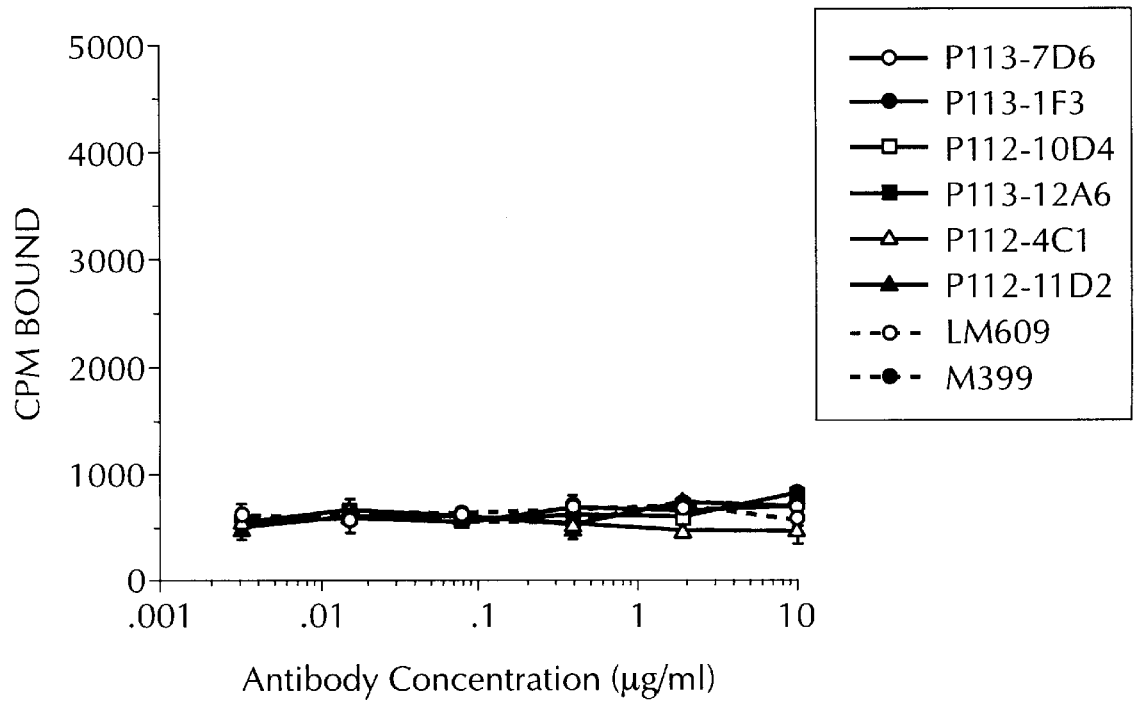

The ligand to which an integrin specifically binds is referred to as a specific ligand, and must necessarily be recited in the context of a particular integrin. Specific ligands for binding to integrins are well characterized for many integrins. For example fibrinogen is a specific ligand for the platelet receptor ($\alpha_{IIb}\beta_{IIIa}$); vitronectin, von Willebrand factor and fibrinogen are specific ligands for the vitronectin receptor (VnR); fibronectin is a specific ligand for the VLA-5 receptor; laminin is a specific ligand for the VLA-6 receptor; and collagen is a specific ligand receptor for the VLA-2 receptor. As indicated in FIG. 1 (panel B), the monoclonal antibodies of the present invention do not bind to $\alpha_{IIb}\beta_{IIIa}$.

A monoclonal antibody composition is typically composed of antibodies produced by clones of a single cell called a hybridoma that secretes (produces) one kind of antibody molecule. Historically, the hybridoma cells are formed by fusing an antibody-producing cell and a myeloma or other self-perpetuating cell line. Such antibodies were first described by Kohler and Milstein, *Nature,* vol. 256 (1975) 495–497, which description is incorporated by reference, although numerous well known variations have since been described for producing hybridoma cells.

The preparation of monoclonal antibodies generally involves immunizing a mammal with an inoculum containing the integrin against which the antibody is to immunoreact, thereby inducing in the mammal antibody molecules having the immunospecificity described herein. The antibody-producing cells are then isolated, cloned and screened for the presence of antibody molecules of interest.

The integrin inhibiting monoclonal antibodies of this invention may be prepared by the method comprising the steps of:

(a) Immunizing an animal with an inoculum comprising an integrin. The integrin can be presented in a variety of forms, as described herein including purified integrin, partially isolated integrin in the form of cell membranes having the cell surface integrin receptor associated with the membranes, and whole cells having the integrin associated with the cell membrane.

The immunization is typically accomplished by administering the inoculum to an immunologically competent mammal in an immunologically effective amount, i.e., an amount sufficient to produce an immune response. Preferably, the mammal is a rodent such as a rabbit, rat or mouse. The mammal is then maintained for a period sufficient for the mammal to produce cells secreting antibody molecules that immunoreact with the receptor.

The word "inoculum" is used herein to describe a composition containing an integrin in one of the forms described above as an active ingredient used for the preparation of integrin-inhibiting antibodies.

The inoculum contains an effective, immunogenic amount of an $\alpha_v\beta_3$ integrin. The effective amount of integrin per unit dose sufficient to induce an immune response to the immunizing integrin depends, among other things, on the species of animal inoculated, the body weight of the animal and the chosen inoculation regimen as is well known in the art. Inocula typically contain protein concentrations of about 10 micrograms to about 500 milligrams per inoculation (dose), preferably about 50 micrograms to about 50 milligrams per dose.

The term "unit dose" as it pertains to the inocula refers to physically discrete units suitable as unitary dosages for animal, each unit containing a predetermined quantity of material calculated to produce the desired immunogenic effect in association with the required diluent; i.e., carrier of vehicle. The specifications for the novel unit dose of an inoculum of this invention are dictated by and are directly dependent on (a) the unique characteristics of the active material and the particular immunologic effect to be achieved, and (b) the limitations inherent in the art of compounding such active material for immunologic use in animals, as disclosed in detail herein, these being features of the present invention.

Inocula are typically prepared from the immunogen, for example an isolated integrin, by dispersing the immunogen in a physiologically tolerable diluent such as water, saline or phosphate-buffered saline to form an aqueous composition.

Inocula can also include an adjuvant as part of the diluent. Adjuvants such as Freund's Complete Adjuvant (FCA), Freund's Incomplete Adjuvant (FIA) and alum are material well known in the art, and are available commercially from several sources.

In a preferred immunization, mice were immunized 3 times over a period of several weeks with $1 \times 10^6$ baby hamster kidney (BHK) cells that had been engineered to produce $\alpha_v\beta3$. BHK cells were transfected using LIPOFECTAMINE (a proprietary composition of 3:1 (w/w) liposome formulation of the polycationic lipid 2,3-dioleyloxy-N-[2(spermine- carboxamido)ethyl]-N,N-dimethyl-1-propanaminiumtrifluoroacetate (DOSPA) and the neutral lipid dioleoyl phosphatidylethanolamine (DOPE) in membrane-filtered water) according to the manufacturer's recommendations (Gibco BRL, Gaithersburg, Md.), with human $\alpha_v$ or $\beta_3$ cDNA in the mammalian expression vector PCDNA3 (Invitrogen Corporation) which confers Neomycin resistance (Southern, P. J. and Berg, P., *J. Mol. Appl. Gen.*, Vol. 1 (1982) 327). Expression of human $\alpha_v\beta3$ by transfected BHK cells was confirmed by flow cytometry using the $\alpha_v\beta_3$-specific mAb LM609 (Chemicon, Temecula, Calif.; *Proc. Natl. Acad. Sci. USA*, Vol. 84 (1987) 6471. Mice were immunized with $\alpha_v\beta_3$-expressing BHK cells emulsified in FCA at the time of the first immunization; all other immunizations utilized antigen mixed with FIA or phosphate buffered saline. Approximately four days prior to harvesting splenocytes from mice immunized with cells, the mice were immunized with $\alpha_v\beta_3$ purified from human placental extracts.

(b) A suspension of antibody-producing cells removed from the immunized mammal is then prepared. This is typically accomplished by removing the spleen of the mammal and mechanically separating the individual spleen cells in a physiologically tolerable medium using methods well known in the art.

(c) The suspended antibody-producing cells are treated with a transforming agent capable of producing a transformed ("immortalized") cell line. Transforming agents and their use to produce immortalized cell (transformed) lines are well known in the art and include DNA viruses such as Epstein Bar Virus (EBV), Simian Virus 40 (SV40), Polyoma Virus and the like, RNA viruses such as Moloney Murine Leukemia Virus (Mo-MuLV), Rous Sarcoma Virus and the like, myeloma cells such as P3X63-Ag8.653, Sp2/0-Agl4 and the like. In preferred embodiments, treatment with the transforming agent results in the production of a hybridoma by means of fusing the suspended spleen cells with mouse myeloma cells from a suitable cell line by the use of a suitable fusion promoter. A preferred ratio is about 2 spleen cells per myeloma cell in a suspension containing about $10^8$ splenocytes. A preferred fusion promoter is polyethylene glycol having an average molecule weight from about 1000 to about 4000 (commercially available as PEG 1300-1600, ATCC); however, other fusion promoters known in the art maybe employed.

The cell line used should preferably be of the so-called "drug resistant" type, so that unfused myeloma cells will not survive in a selective medium, while hybrids will survive. A common class is 8-azaguanine resistant cell lines, which lack the enzyme hypoxanthine-guanine phosphoribosyl transferase and hence will not be supported by HAT (hypoxanthine, aminopterin, and thymidine) medium. It is also generally preferred that the myeloma cell line used be of the so-called "non-secreting" type which does not itself produce any antibody. In certain cases, however, secreting myeloma lines may be preferred.

(d) The transformed cells are then cloned, preferably to monoclonality. The cloning is preferably performed in a tissue culture medium that will not sustain (support) non-transformed cells. When the transformed cells are hybridomas, this is typically performed by diluting and culturing in separate containers the mixture of unfused spleen cells, unfused myeloma cells, and fused cells (hybridomas) in a selective medium which will not sustain the unfused myeloma cells (non-transformed cells). The cells are cultured in this medium for a time sufficient to allow death of the unfused cells (about one week). The dilution can be a limiting dilution, in which the volume of diluent is statistically calculated to isolate a certain number of cells (e.g., 1–4) in each separate container (e.g., each well of a microtiter plate). Alternatively, the dilution may be done in soft agar such that a single cell suspension is generated and then plated in semisolid agar (Goding, J. W.,*J. Immunol. Methods.*, Vol. 39 (1980) 285). The medium is one (e.g., HAT medium) that will not sustain the drug-resistant (e.g., 8-azaguanine resistant) unfused myeloma cell line.

(e) The tissue culture medium of the cloned hybridomas is then assayed to detect the presence of secreted antibody molecules having the immunoreactive properties as described herein using well known immunological screening techniques together with the assays described herein to identify integrin-inhibiting antibodies.

As shown by the various screening protocols in Example 1, below, to identify integrin-inhibiting antibodies, several separate assays are typically conducted to identify an antibody of this invention. First, the culture is evaluated for antibodies immunoreactive with $\alpha_v\beta_3$. Hybridoma in cell cultures containing the cult-reactive antibodies are then cloned by dilution and individual clones re-screened to identify clonal cell lines producing $\alpha_v\beta_3$-reactive antibodies.

Representative and preferred methods for producing integrin-inhibiting monoclonal antibody compositions are described in Example 1, below.

(f) Desired clonal cell lines are then selected. To produce a much greater concentration of monoclonal antibody, the desired hybridoma can be transferred by injection into mice, preferably syngeneic or semisyngeneic mice. The hybridoma will cause formation of antibody-producing tumors after a suitable incubation time, which will result in a high concentration of the desired antibody (about 5–20 mg/ml) in the bloodstream and peritoneal exudate (ascites) of the host mouse.

A monoclonal antibody composition can be enriched in the desired antibody molecules by additional isolation methods such as immunoaffinity chromatography using solid phase affixed immunizing antigens, as described herein, or by using, for example, DEAE Sephadex to obtain the IgG fraction, if desired.

Media and animals useful for the preparation of these compositions are both well known in the art and commercially available and include synthetic culture media, inbred mice and the like. An exemplary synthetic medium is Dulbecco's minimal essential medium (DME/FIZ, 1:1) supplemented with 4.5 gm/l glucose, 20 mM glutamine, and 20% fetal calf serum. An exemplary inbred mouse strain is the BALB/c.

A monoclonal antibody composition can also be produced by methods well known to those skilled in the art of producing antibodies by recombinant DNA methods. Those methods include isolating, manipulating, and expressing the nucleic acid that codes for all or part of an immunoglobulin variable region including both the portion of the variable region comprised by the variable region of immunoglobulin light chain and the portion of the variable region comprised by the variable region of immunoglobulin heavy chain. Methods for isolating, manipulating, and expressing the variable region coding nucleic acid in procaryotic and eucaryotic hosts are disclosed in Robinson et al., PCT Publication No. WO 89/0099; Winter et al., European Patent Publication No. 0239400; Reading, U.S. Pat. No. 4,714,681; Cabilly et al., European Patent Publication No. 0125023; Sorge et al., *Mol. Cell Biol.,* Vol. 4 (1984) 1730–1737; Beher et al., *Science, Vol.* 240 (1988) 1041–1043; Skerra et al., *Science,* Vol. 240 (1988) 1030–1041; and Orlandi et al., *Proc. Natl. Acad. Sci.,* U.S.A., Vol. 86 (1989) 3833–3837. Typically the nucleic acid codes for all or part of an immunoglobulin variable region that binds a preselected antigen (ligand.) Sources of such nucleic acid are well known to one skilled in the art and, for example, may be obtained from a hybridoma producing a monoclonal antibody that binds the preselected antigen, or the preselected antigen may be used to screen an expression library coding for a plurality of immunoglobulin variable regions, thus isolating the nucleic acid.

See, for example, the method of isolating monoclonal antibodies from an immunological repertoire as described by Sastry et al., (*Proc. Natl. Acad. Sci.,*Vol. 86 (1989) 5728–5732); and Huse et al., (*Science,* Vol. 246 (1989) 1275–1281).

Isolated nucleic acid coding for the murine immunoglobulin genes may be engineered to prepare $\alpha_v\beta_3$ antibody combining regions grafted into human Ig backbones using the process known as antibody humanization (Richmann et al., *Nature,* Vol. 332 (1988) 323). Further, nucleic acid coding for the murine immunoglobulin genes of $\alpha_v\beta_3$ antibodies may be engineered to produce recombinant bifunctional antibodies, single chain Fv (scFv) or bispecific scFv fusion proteins that, in a single gene or gene product, combine a toxin, immunostimulatory molecule or targeting moiety with the $\alpha_v\beta_3$-binding domain (Reisfeld, et al., *Curr Top Microbiol Immunol,* Vol. 213 (1996) 27; Rybak et al., *Proc. Nati. Acad. Sci.* USA, Vol. 89 (1992) 3165; Siegall et al., *J. Immunol.,* Vol. 152 (1994) 2377; Naramura, et al., *Immunol. Lett.,* Vol. 39 (1993) 91). Further, nucleic acid coding for the murine immunoglobulin genes of $\alpha_v\beta_3$ antibodies or the nucleic acid coding the humanized engrafted counterpart may be engineered to increase antigen-binding affinity using techniques known to those skilled in the art (Rheinnecker et al., *J. Immunol.,* Vol. 157 (1996) 2989; Barbas et al., *TBTECH,* Vol. 14 (1996) 230; Hoogenboom, *Trends Biotechnol.* Vol. 15(2) (1997) 62). Recombinant $\alpha_v\beta_3$ antibodies, antibody fragments or fusion proteins derived from the same may b e expressed in *E coli,* transgenic plants or animals (Huse et al., *Science,* Vol. 24G (1989) 1275; Hiatt et al., *Nature,* Vol. 342 (1989) 76; Morcol et al., *Ann. N. Y. Acad. Sci.,* Vol. 721 (1994) 218; Ebert et al., *Biotechnology-N-Y,* Vol. 9 (1991) 835).

The anti-$\alpha_v\beta_3$ monoclonal antibodies of the present invention may be made by recombinant DNA methods, such a those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be inserted in to an expression vector, and then transfected into host cells such as simian COS cells, Chinese hamster ovary (CHO) cells, or myeloma cells that do not otherwise produce immunoglobulin protein, to obtain the synthesis of monoclonal antibodies in the recombinant host cells.

The DNA also may be modified, for example, by substituting the coding sequence for human heavy and light chain constant domains in place of the homologous murine sequences (see Morrison et al., *Proc. Natl. Acad. Sci. USA* 81:6851–6855, U.S. Pat. No. 4,816,567 and U.S. Pat. No. 5,693,761, which are incorporated by reference herein). Recombinant DNA technology has been used to produce immunoglobulin molecules that have human framework regions combined with complementarity determining regions (CDR's) from a donor mouse or rat immunoglobulin. These new proteins are called "reshaped" or "humanized" immunoglobulins and the process by which the donor immunoglobulin is converted into a human-like immunoglobulin by combining its CDR's with a human framework is called "humanization". Humanized antibodies are important because they bind to the same antigen as the original antibodies, but are less immunogenic when injected into a human host.

The monoclonal antibody compositions produced by the above method can be used, for example, in diagnostic and therapeutic modalities wherein specific binding or inhibition of integrin is desired, as described further herein.

Figure 2:
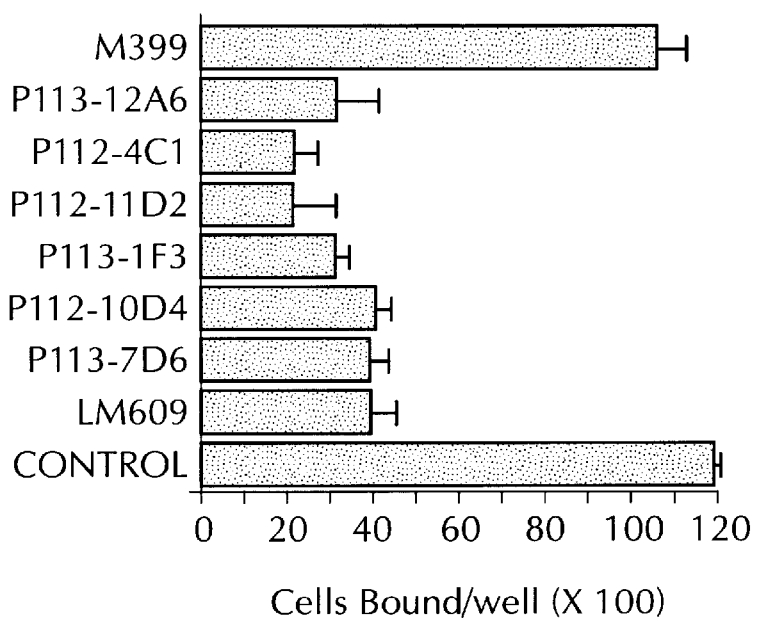
FIG. 2 shows that monoclonal antibodies (50 μg/ml) P113-7D6, P112-4C1, P113-12A6, P112-llD2, P112-10D4, P113-lF3, LM609, but not a control monoclonal antibody M399, inhibit Mn-induced binding of M21 (a melanoma cell line) cells to fibrinogen.
Figure 3:
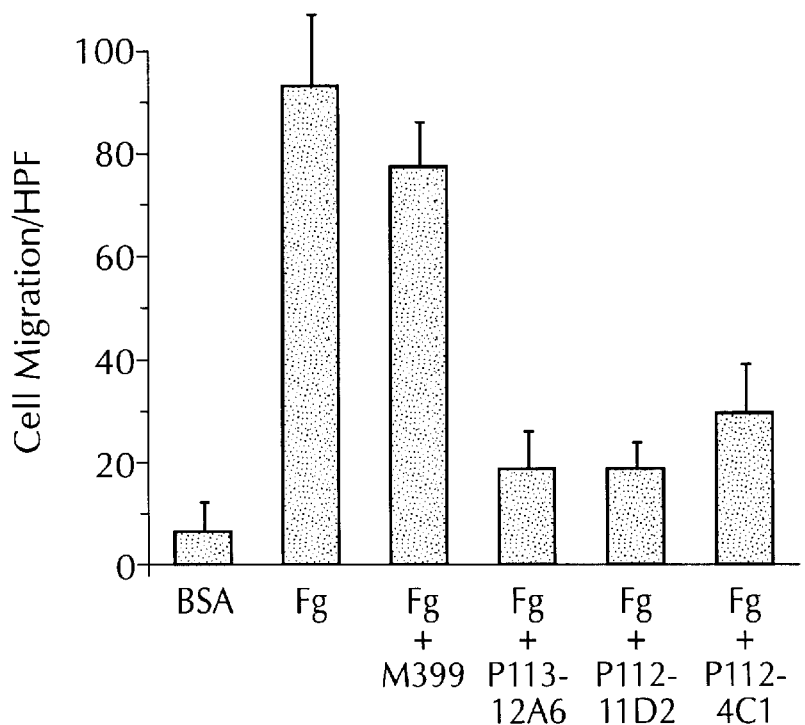
FIG. 3 shows that the monoclonal antibodies (50 μg/ml) P112-4Cl, P113-12A6, P112-llD2, but not the control monoclonal antibody M399, inhibit M21 cell (a human melanoma cell line) migration toward fibrinogen (Fg). This figure shows migration to Fg alone and Fg in the presence of antibody.
Figure 4:
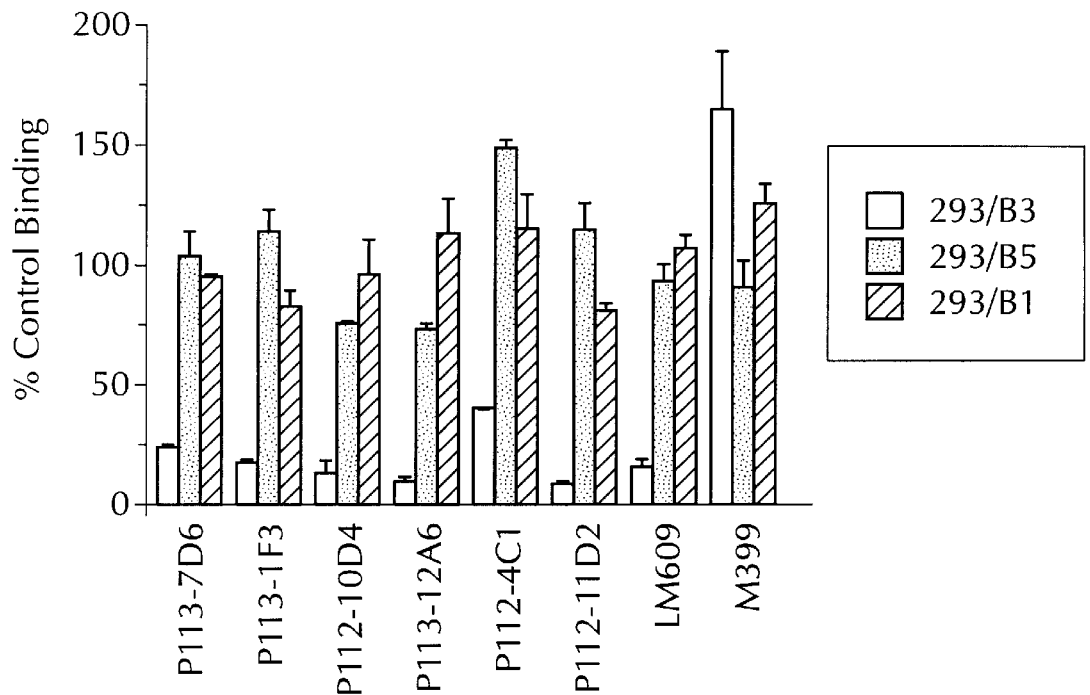
FIG. 4 shows that monoclonal antibodies (50 μg/ml) P113-7D6, P112-4C1, P113-12A6, P112-llD2, P112-10D4, P113-1F3 and LM609 inhibit 293/B3, but not 293/B5 or 293/B1, cell adhesion to vitronectin.
Figure 5:
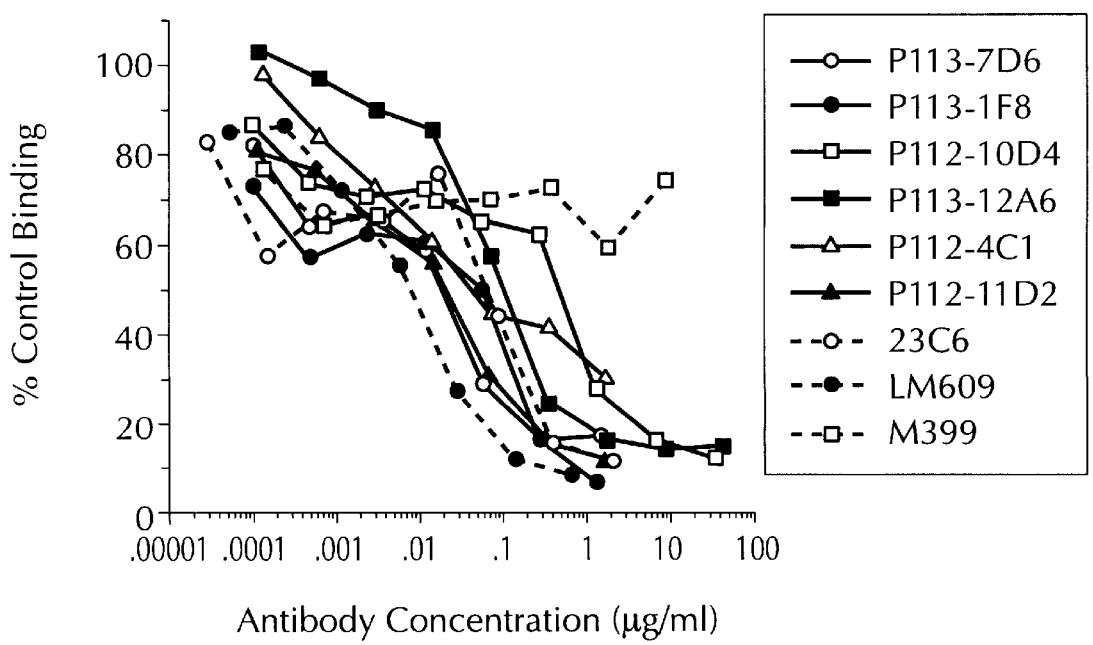
FIG. 5 shows that monoclonal antibodies P113-7D6, P112-4C1, P113-12A6, P112-llD2, P112-10D4, P113-1F3, 23C6 and LM609 inhibit 293/B3 cell adhesion to vitronectin. M399 is a control monoclonal antibody. 23C6 antibody was purchased from PharMingen (San Diego, Calif.).
Figure 6:
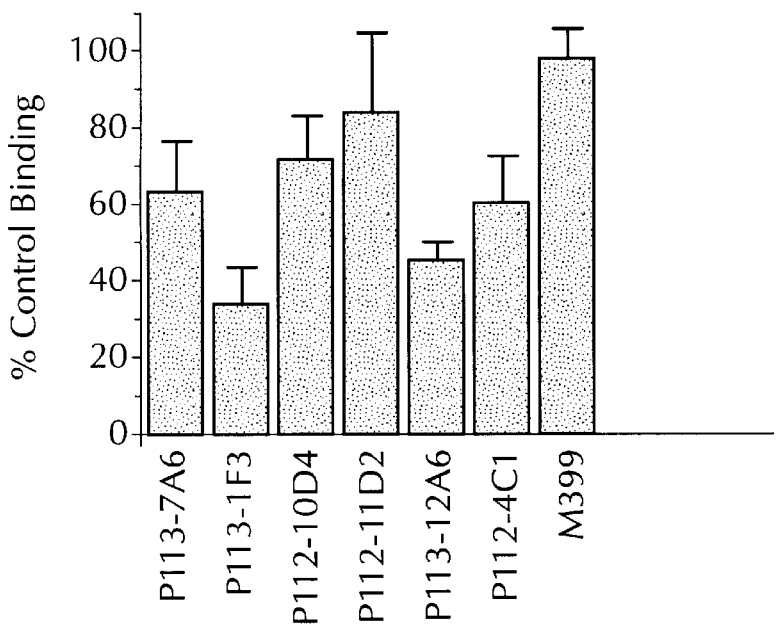
FIG. 6 shows that monoclonal antibodies (50 μg/ml) P113-7D6, P112-4C1, P113-12A6, P112-llD2, P112-1OD4, P113-1F3 inhibit rabbit osteoclast adhesion to osteopontin. M399 is a control monoclonal antibody.
Figure 7:
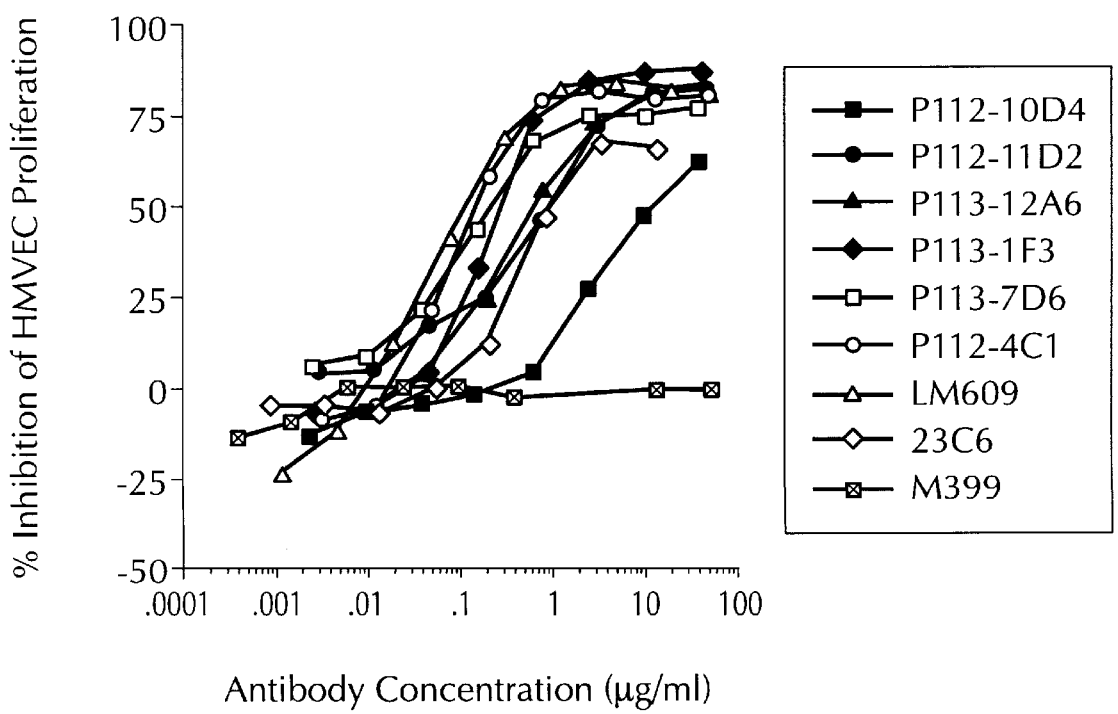
FIG. 7 shows that the monoclonal antibodies P113-7D6, P112-4C1, P113-12A6, P112-llD2, P112-10D4, LM609, 23C6 inhibit the proliferation of human dermal microvascular endothelial cells plated on osteopontin. The control monoclonal antibody, M399, has no inhibitory activity.
Figure 8:
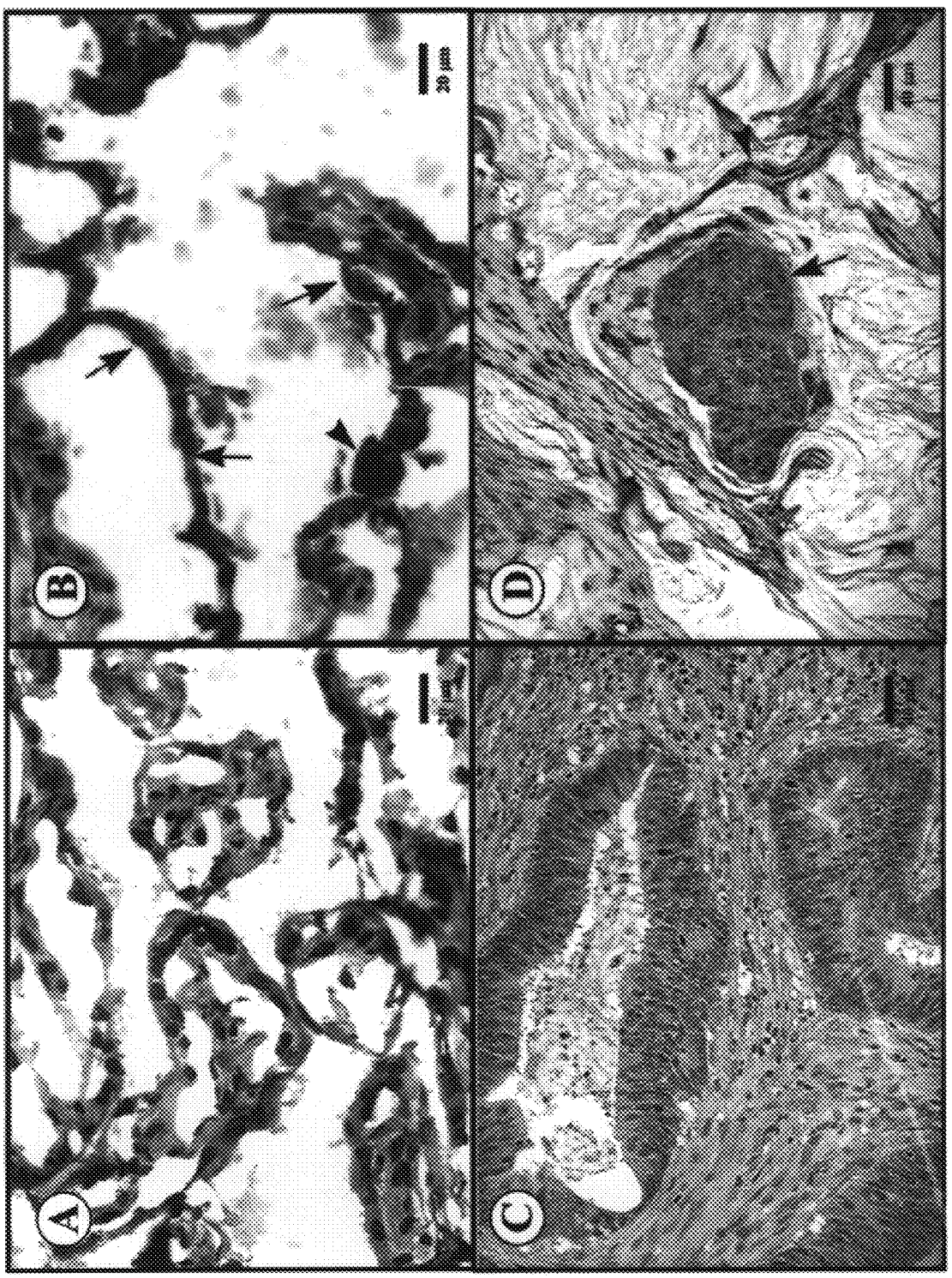
FIG. 8 shows immunolocalization of $\alpha_v\beta_3$ in human placenta tissue and human colon carcinoma tissue with monoclonal anti-$\alpha_v\beta_3$ P112-4C1. Panels A and B are photomicrographs of a section of human placenta that had been frozen, sectioned and stained for detection of the $\alpha_v\beta_3$ integrin. Panel A shows that staining of the placental tissue using an irrelevant isotype-matched antibody control fails to detect the presence of $\alpha_v\beta_3$. Panel B shows that staining the placental tissue using the monoclonal anti-$\alpha_v\beta_3$ P112-4C1 antibody detects trophoblasts (arrows) and syncytiotrophoblasts (arrowhead) that are positively stained for the presence of the $\alpha_v\beta_3$ integrin. Panels C and D are photomicrographs of portions of a section of formalin-fixed, paraffin-embedded human clonic carcinoma that had been processed, sectioned and stained for detection of the $\alpha_v\beta_3$ integrin. Panel C shows that staining of the human colon carcinoma tissue using an irrelevant isotype matched antibody control fails to detect the presence of $\alpha_v\beta_3$. Panel D shows that the monoclonal anti-$\alpha_v\beta_3$ P112-4C1 antibody detects positive staining in neoplastic enterocytes (arrow), endothelial cells (arrowhead) and fibroblasts (open arrowhead) in human colon carcinoma tissue.

(g) IgG isolated from ascites fluids of mice inoculated with the cell lines producing $\alpha_v\beta_3$-reactive antibodies are then further evaluated as inhibitors of $\alpha_v\beta_3$ in assays such as inhibition of Mn-induced binding of M21 cells to fibrinogen (FIG. 2); inhibition of M21 cell migration (FIG. 3); inhibition of 293/$\beta_3$, 293/$\beta_5$ or 293/$\beta_1$ cells to vitronectin (FIGS. 4 and 5); and inhibition of rabbit osteoclast adhesion to osteopontin (FIG. 6).

Hybridomas

Hybridomas of the present invention are those which are characterized as having the capacity to produce an integrin-inhibiting monoclonal antibody composition of this invention.

A preferred hybridoma of the present invention is characterized as producing integrin-inhibiting antibody molecules that immunoreact with an integrin. The antibody also is "complex-specific" in the sense that it immunoreacts with an integrin $\alpha_v\beta_3$ complex and does not react with either of the integrin $\alpha_v$ or $\beta_3$ subunits individually. In other words, the antibody recognizes $\alpha_v$ in the context of $\beta_3$, while at the same time recognizing $\beta_3$ in the context of $\alpha_v$, as shown in FIG. 5.

Representative preferred hybridomas are prepared and described in Example 1, below. Particularly preferred are the hybridoma cell lines designated P113-7D6, P112-4C1, P113-12A6, P112-llD2, P112-lOD4 and P113-1F3.

Hybridoma cell lines P113-7D6, P112-4C1, P113-12A6, P112-llD2, P112-lOD4 and P113-IF3 have been deposited pursuant to Budapest Treaty requirements with the American Type Culture Collection (ATCC), 10801 University Blvd., Manassas, Va., 20110-2209, U.S.A., on Nov. 5, 1996, and were assigned, respectively, accession numbers HB-12224, HB-12225, HB-12226, HB-12227, HB-12228 and HB-12229.

These hybridomas were deposited in a depository affording permanence of the deposit and ready accessibility thereto by the public upon the grant of a patent, under conditions which assure that access to the hybridoma will be available during the pending of the patent application to those entitled to such access, and that all restrictions on the availability to the public of the hybridoma as deposited will be irrevocably removed upon the granting of the patent. The deposited hybridomas will be maintained by the ATCC, and all maintenance fees have been paid, for the term of the patent or 30 years from the date of deposit, whichever is longer, and in all events for at least five years after the date of the last request for access.

Methods for producing hybridomas producing (secreting) antibody-molecules having a desired immunospecificity, i.e., having the ability to immunoreact with a particular antigen, an identifiable epitope on a particular antigen, are well known in the art and are described further herein. Particularly applicable is the hybridoma technology described by Niman et al., *Proc. Natl. Acad. Sci. USA,* Vol. 80 (1983) 4949–4953, and by Gaifre et al., *Meth. Enzymol.,* Vol. 73 (1981) 3–46, which descriptions are incorporated herein by reference.

Therapeutic Methods and Compositions

Therapeutic methods and compositions are contemplated for inhibiting integrins. These methods are useful to inhibit cell attachment and migration mediated by the integrins and find application in a wide variety of cell types, tissues and systems where attachment of cells is desired.

Thus in general the invention contemplates a method for inhibiting an integrin that binds a specific ligand comprising contacting the integrin with a solution containing an inhibiting amount of an integrin-inhibiting antibody as described herein that is immunospecific for the integrin, for example $\alpha_v\beta_3$ integrin.

Typically the method is practiced on cells expressing the integrin on the surface of the cell, so the contacting occurs by admixing the cells in a solution with the integrin-inhibiting antibodies to form an admixture. The admixture is preferably physiologically compatible with cell viability, preferably sterile, and more preferably compatible with admixture with blood to facilitate adding the admixture to the blood.

An inhibiting amount of integrin-inhibiting antibody is an amount sufficient to produce the desired result, namely to inhibit the integrin to a degree sufficient to reduce the adhesion of the cell expressing the integrin, and typically depends on the amount of integrin to be contacted.

In preferred embodiments, whether the method is practiced in vitro or in vivo, an inhibiting amount is an amount sufficient to provide at least about one molar equivalent of integrin-inhibiting antibody per molar equivalent of integrin to be inhibited. This amount is referred to as a stoichiometric amount of integrin-inhibiting antibody. Although antibody affinity for immunoreaction is typically sufficient for an integrin-inhibiting antibody to immunoreact stoichiometrically in dilute solutions, it is preferred that an inhibiting amount is in the range of about 100 nanomolar (i) to 1 millimolar (mM) preferably in the range of 1 to 100 micromolar ($\mu$M) and more preferably about 1 to 10 $\mu$M.

When an integrin-inhibiting method is practiced in vitro, a liquid sample containing integrin, and preferably a physiological fluid containing cells that express cell surface integrin, are admixed with an inhibiting amount of an integrin-inhibiting antibody of this invention to form a complex. The complex is maintained under biological conditions compatible with the formation of an immunoreaction product and also compatible, if required, with cell viability for a time period sufficient for the integrin-inhibition antibody to immunoreact with the integrin and, when immunoreacted, inhibit the integrin.

When the integrin-inhibiting method is practiced in vivo, an inhibiting amount of an antibody composition containing a physiologically tolerable diluent and integrin-inhibiting antibody molecules as described herein is intravenously administered to a mammal, e.g. a human, and the mammal is maintained for a sufficient period to allow the antibody molecules to immunoreact with any integrin present and form an inhibiting immunoreaction product. Other routes of administration are envisioned, including intraperitoneal, intra muscular, intrathecal and subcutaneous.

In preferred embodiments, a therapeutic composition for use in an integrin-inhibiting method includes integrin-inhibiting antibody molecules that immunoreact with the integrin complex, i.e., immunoreact with both the $\alpha$ and $\beta$ subunits of the heterodimer of the integrin, but not with just one or the other of the subunits. Exemplary compositions comprise one or more of the monoclonal antibodies secreted by the hybridomas P113-7D6, P112-4C1, P113-12A6, P112-11D2, P112-IOD4 or P113-1F3.

The integrin-inhibiting antibodies may be combined with other pharmaceutical compositions and/or excipients.

For example, $\alpha_v\beta_3$ antibody may be co-administered or added to established anti-cancer chemotherapeutic or biotherapeutic regimens. Normal physiologic saline is a preferred excipient or vehicle for administration of antibody. This may include, but is not limited to, combining or co-administering $\alpha_v\beta_3$ antibodies with cytotoxic drugs, combinations of cytotoxic drugs or with immune stimulating drugs, such as interleukins or their derivatives or with hematopoietic factors and their derivatives. For example, $\alpha_v\beta_3$ antibody may be co-administered or added to therapeutic regimens for the use IL-1, IL-2, IL-4, IL-6, IL-12, IL-15, TNF, $\alpha$, $\beta$, $\gamma$ interferons and M-CSF, or combinations of these agents or their derivatives, in biologic therapy of cancer. Further, $\alpha_v\beta_3$ antibody may be co-administered or added to therapeutic regimens for the use of G-CSF, M-CSF, IL-3 and erythropoietin, or combinations of these agents or their derivatives, in biologic therapy of cancer. The anti-$\alpha_v\beta_3$ monoclonal antibodies of the present invention, or fragments thereof containing a paratope (e.g., Fab, Fab', F(ab')2 and F(v) fragments), may also be combined with cytotoxic or cytostatic drugs, protein toxins, nucleic acids or radioisotopes by methods well know to those of ordinary skill in the art. Depending on the dose and the nature of the antibody conjugate, it is possible to either kill tumor cells and reduce tumor size or achieve inhibition of cell growth and hence inhibit tumor growth.

Many monoclonal antibody conjugates of radioisotopes, protein toxins, cytotoxic and cytostatic drugs have been prepared and tested in model systems. Radio-labelled monoclonal antibody conjugates have proven to be effective imaging agents in the clinic and are showing promising therapeutic results for the treatment of lymphomas and leukemias in humans. Protein toxin monoclonal antibody conjugates are also being tested in human clinical trials for conditions such as lymphomas. Cytotoxic and cytostatic drugs conjugated to antibodies have also been investigated in clinical trials.

Exemplary procedures for linking cytotoxic and cytostatic drugs, as well as protein toxins and peptides, to antibodies are described in the *CRC Handbook: Chemistry of Protein Conjugation and Cross-linking,* Chapter 11, 267 (CRC Press Inc., Boca Raton Fla., 1993), as well as in, for example, U.S. Pat. No. 5,591,829; both of which are incorporated by reference herein.

The amino side chains of lysines, the amino terminal group in polypeptides, the carboxyl groups of aspartic and glutamic acids, the thiol group of cysteins, and the carbohydrate moiety of antibodies, toxins and other drugs have been used to prepare drug conjugates. *The CRC Handbook: Chemistry of Protein Conjugation and Cross-linking* describes, among other things, various heterobifunctional reagents for linking various substances to antibodies. Such reagents include m-maleimido-benzoyl-N-hydroxysuccinimide ester (MBS) and N succinimidyl-3-(2-pyridyldithio)propionate (SPDP). Disulfide generating agents, such as 3-(2-dipyridyldithio)propionate can be used to generate pyridyl disulfide groups in proteins in conjunction with water soluble carbodiimides such as ethyl-3-(3-dimethylaminopropyl carbodiimide. Conjugation through thioether linkages can be effected using iodoacetyl compounds, such as N-hydroxysuccinimidyl iodoacetate or N-succinimidyl(4-iodoacetyl)aminobenzoate, while conjugation can also be achieved using acid-labile and photocleavable cross-linkers, such as 4(iodoacetylamino)-3,4,5,6-tetrahydrophthalic anhydride and 1-[4-nitro-3-(1-chlorocarbonyloxyethyl)phenyl]methyl-S-acetylthioic acid ester. Coupling can also be effected through carbohydrate residues or linkers, such as dextrans, as well as with polyamino acids, such as poly-L-glutamate.

Various protein toxins, plant toxins, peptides and cytotoxic and cytostatic compounds for conjugation to antibodies include: ricin, abrin, modeccin, gelonin, pokeweed antiviral protein (PAP), $\alpha$-amanitin, ribosome inhibiting protein (RIP), barley RIP, wheat RIP, corn RIP, flax RIP, bacterial toxins including diphtheria toxin, fragments of diphtheria toxin, pseudomonas exotoxin, shiga toxin and chemical toxins including nitrogen mustard, taxol, doxorubicin, daunomycin, methotrexate, cisplatin, bleomycin, vinblastine, mitomycin C, idarubicin, morpholinodoxorubicin, melphalan, cytosine arabinoside, 5-fluorouracil, and neocarzinostatin.

For example, SPDP could be used to link free amino groups of antibodies or fragments thereof containing a paratope (such as Fab, Fab', F(ab')2 and F(v) fragments) to a variety of plant toxins including ricin, abrin, modeccin, gelonin, pokeweed antiviral protein (PAP), $\alpha$-amanitin, ribosome inhibiting protein (RIP), barley RIP, wheat RIP, corn RIP, flax RIP, bacterial toxins including diphtheria toxin, fragments of diphtheria toxin, pseudomonas exotoxin, shiga toxin and chemical toxins including methotrexate, nitrogen mustard, doxorubicin and daunomycin.

One of ordinary skill in the art can readily prepare antibody conjugates of the following compounds using the antibodies of the present invention: mitomycin C, doxorubicin and daunomycin (Suzuki et al., *Chem. Pharm. Bull.,* Vol. 29 (1981) 844, incorporated by reference herein); idarubicin (Pietersz et al., *Cancer Res.,* Vol. 48 (1988) 926, incorporated by reference herein); doxorubicin (Trail et al., *Cancer Res.,* Vol. 52 (1992) 5693; Trail et al., *Science,* Vol. 261 (1993) 212; Aboud-Pirak et al., *Proc. Natl. Acad. Sci. USA,* Vol. 86 (1989) 3778, incorporated by reference herein); morpholinodoxorubicin (Mueller et al., *Bioconjugate Chem.,* Vol. 1, (1990) 325; Dillman et al., *Cancer Res.,* Vol. 48 (1988) 6097); daunomycin (Hurwitz et al., *Cancer Res.* Vol. 35 (1975) 1175; Page et al., *Proc. Am. Assoc. Cancer Res.,* Vol. 22 (1981) 211; Page et al., "Drug targeting with monoclonal antibodies", in *Protides of the Biological Fluids,* Peeters, H., Ed., Vol. 29, Pergammon Press, Oxford, (1981) 933; Tsukada et al., *J. Natl. Cancer Inst.,* Vol. 73 (1984) 721; Suzuki et al., *Chem. Pharm. Bull.,* Vol. 29 (1981) 844; Hurwitz, et al., *Eur. J. Cancer,* Vol. 14 (1978) 1213; Hurwitz et al., *J. Appl. Biochem.,* Vol. 2, (1980) 25; Lavie et al., *Cancer Immunol. Immunother.,* Vol. 33 (1991) 223; Dillman et al., *Cancer Res.,* Vol. 48 (1988) 6097, incorporated by reference herein); vinblastine (Apelgren et al., *Cancer Res.* Vol. 50 (1990) 3540; Starling et al., *Cancer Res.,* Vol. 51 (1991) 2965; Johnson et al., *Cancer Immunol. Immunother.,* Vol. 27 (1988) 241, incorporated by reference herein); melphalan (Smyth et al., *Cancer Res.,* Vol. 47 (1987) 62, incorporated by reference herein); cytosine arabinoside and 5-fluorouracil (Hurwitz et al., *J. Med. Chem.,* Vol. 28 (1985) 137, incorporated by reference herein); bleomycin (Manabe et al., *Biochem. Biophys. Res. Commun.,* Vol. 115 (1983) 1009, incorporated by reference herein); neocarzinostatin (Kimura et al., *Cancer Immunol. Immunother.,* Vol. 7, (1980) 235, incorporated by reference herein); cisplatin (McIntosh et al., *J. Pharm. Sci.,* Vol. 86(12) (1997) 1478, incorporated by reference herein); methotrexate (Kulkarni et al., *Cancer Res.,* Vol. 41 (1981) 2700, incorporated by reference herein).

Recently, various types of oligodeoxynucleotides ("ODNs") have demonstrated a broad array of activities against distinct intracellular targets, such as oncogenes, normal host genes, and viral targets. Uhlmann et al., *Chem. Rev.*, Vol. 90 (1990) 543; Crooke, *Biotechnology*, Vol. 10 (1992) 882, incorporated by reference herein. Chemically modified nuclease resistant analogs of ODNs have been shown to display activity at relatively high concentrations (greater than 1 $\mu$M), whereas unmodified phosphodiester ODNs have activities at typically greater than 10 $\mu$M. Complexation of ODNs to anti-$\alpha_v\beta_3$ integrin antibodies offers an approach to facilitate delivery of ODNs to targets sites, such as mammalian (e.g. human) cells expressing $\alpha_v\beta_3$ integrin. Such compositions may be made by linking polypeptide sequences which bind ODNs, such as the nucleocapsid 7 of HIV-1 or nucleocapsid-derived peptides, for example: [SEQ ID 1],

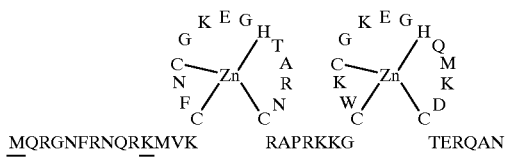

or SEQ ID 2],

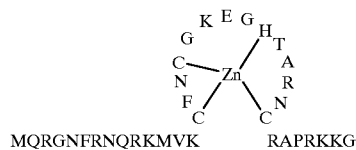

to the antibody. Suitable nucleocapsid 7 peptides, as well as suitable oligonucleotides (including anti-sense oligonucleotides, e.g., as in SEQ ID 3, for c-myb specific MrRNA), are identified in Bachmann et al., *J. Mol. Med.*, Vol. 76 (1998) 126, which is incorporated by reference herein. The nucleocapsid 7 peptides can be made by methods well known in the art and linked to antibodies of the present invention as described in the *CRC Handbook: Chemistry of Protein Conjugation and Cross-linking*, Chapter 11 (CRC Press Inc., Boca Raton Fla.) for linking proteins and peptides to antibodies.

In place of oligonucleotides, it may be desireable to substitute anti-sense single stranded DNA of a gene, such as the HIV-or herpes symplex virus thymidine kinase (TK) gene, which are described in Wagner et al., *Proc. Natl. Acad. Sci. USA*, Vol. 78 (1981) 1441 and in U.S. Pat. No. 5,631,236, incorporated by reference herein. Delivery of anti-sense DNA in such a case may be beneficial in the treatment of viral infection, especially against HIV. Alternatively, it may be advantageous to deliver complete double stranded DNA encoding for a gene, instead of the oligonucleotide. For example, the TK gene may be delivered to cells as part of gene therapy for treating solid tumors bearing $\alpha_v\beta_3$ Integrin. In such case, it is envisioned that subsequently a prodrug which is activated by TK, such as ganciclovir, is administered to the individual so as to activate the prodrug.

Recently, antibody-radionuclide compositions have shown success in diagnostic and therapeutic applications in mammals, and especially in humans. In general, conjugated antibody-radionuclide compositions involve chemically reacting a chelating agent, which can bind the radionuclide, to the antibody. Numerous chelating agents are known in the art for this purpose and generally have nitrogen and sulfur donor atoms, such as dithiodiaminocarboxylic acids and dithioamidocarboxylic acids (known as $N_2S_2$ chelating agents) and thiotriaza chelating compounds (known as $N_3S$ chelating agents). Suitable radioisotopes and chelating agents, along with methods for linking the same to antibodies, are disclosed in U.S. Pat. No. 5,130,118, which is incorporated by reference herein. Alternatively, radiohalogen labelled compounds can be made and reacted with antibody, as described in U.S. Pat. No. 5,679,318 and 5,252,748, which are incorporated by reference herein. Exemplary procedures and compounds for making radiolabelled monoclonal antibody conjugates for radionuclides such as $^{186}$Re, $^{188}$Re, $^{153}$Sm, $^{90}$y, $^{105}$Rh, $^{131}$I are disclosed in U.S. Pat. No. 5,679,318. Similarly, exemplary procedures and chelating compounds for making radiolabelled monoclonal antibody conjugates for radionuclides of copper, e.g. $^{64}$Cu, $^{67}$Cu; technetium, e.g., $^{99m}$Tc; rhenium, e.g., $^{186}$Re and $^{188}$Re; lead, e.g., $^{203}$Pb and $^{212}$Pb; palladium, e.g., $^{103}$Pd, $^{109}$Pd; bismuth, e.g., $^{212}$Bi and gold, e.g., $^{198}$Au are disclosed in U.S. Pat. No. 5,681,927, which is incorporated by reference herein. One of ordinary skill in the art will appreciate that other isotopes of iodine can also be employed, for example $^{125}$I, and other isotopes, for example $^{241}$Am, $^{192}$Ir, and $^{111}$n, see e.g., U.S. Pat. No. 5,130,118, incorporated by reference herein. Procedures for generation of free sulfhydryl groups on antibodies or antibody fragments are also known, see, e.g., U.S. Pat. No. 4,659,839, which is incorporated by reference herein. Because some radionuclides have relatively short half-lives, it may be desirable to prepare chelating-agent-conjugated antibody and then, shortly prior to use, react the chelating compound conjugated-antibody with the radionuclide of interest.

The Examples which follow are intended as an illustration of certain preferred embodiments of the invention, and no limitation of the invention is implied.

EXAMPLES

Generation of Monoclonal Antibody

Example 1: Production of P112-4C1-A2-C7-A3.

In accordance with the present invention there is disclosed a hybridoma cell line, P112-4C1-A2-C7-A3, produced by hybrid cell line, P112-4C1-A2-C7-A3, generated from a mouse immunized with human $\alpha_v\beta_3$. A sample of this cell line is deposited with the American Type Culture Collection (ATCC), 10801 University Blvd., Manassas, Va., 20110-2209 Rockville, Md. 20852, USA with accession No. HB-12225. This antibody was produced as follows.

Six week old female BALB/c mice were immunized intraperitoneally (i.p.) with 1×10$^6$ BHK cells transfected with $\alpha_v\beta_3$ (BHK/$\alpha_v\beta_3$) in Freund's Complete Adjuvant (FCA). Three weeks later the mice were given a booster i.p. immunization using 1×10$^6$ BHK/$\alpha_v\beta_3$ cells in Freund's Incomplete Adjuvant (FIA). Two weeks later the mice were given a second i.p. booster of 1×10$^6$ BHK/$\alpha_v\beta_3$ cells in FIA. After an additional 3 weeks 5 $\mu$g purified $\alpha_v\beta_3$ in saline was given intravenously and i.p. Fusions were performed 3 days later.

Immunized mice were sacrificed by $CO_2$ overdose and a splenectomy performed immediately. The spleen cells from mice were fused with myeloma P3X63 Ag8.653 (ATCC) using polyethylene glycol, MW 1300–1600 (ATCC). The cells were diluted to 1×10$^6$ cells/ml in HAT selection media, plated in 48 well culture dishes at 0.5 ml/well and grown under selective conditions (HAT medium) that allow only cells resulting from the fusion of a splenocyte with a myeloma cell to proliferate. Five hundred and seventy wells were plated with cells and 225 showed hybridoma growth. Conditioned media of wells with hybridoma growth were screened for the presence of antibodies that bind $^{125}$I-labeled $\alpha_v\beta_3$ or $^{125}$I-labeled labeled $\alpha_{IIb}\beta_{IIIa}$ using the capture assay described below. Ten wells, one of which was well C1 in plate 4 and hence the designation P112-4C1, contained cells that produced an antibody that bound $\alpha_v\beta_3$ but not $\alpha_{IIb}\beta_{IIIa}$. Cells in well 4 C1 were cloned in soft agar in order to obtain colonies of cells derived from a single cell that produces an antibody that absorbs $^{125}$I-labeled $\alpha_v\beta_3$ from solution. Colonies were picked from soft agar, grown in appropriate cell culture media and then rescreened in the $\alpha_v\beta_3$ capture assay. An $\alpha_v\beta_3$-binding colony derived from well A2 was identified and designated P112-4C 1-A2 . This process was repeated two additional times to arrive at the final clonally derived cell line designated P112-4C1-A2-C7-A3. The monoclonal antibody produced by this cell line is an IgG1, κ.

IgG was purified from mouse ascites generated with the P112-4C1-A2-C7-A3 cell line by Protein G or Protein A chromatography as described below and the purified P112-4C1-A2-C7-A3 monoclonal antibody (mAb) tested in various assays to further characterize the properties of the P112-4CI-A2-C7-A3 as an inhibitor of $\alpha_v\beta_3$. Representative examples of the results of these type of assays are shown in FIGS. 1–7.

Purification of Monoclonal Antibody

Ascites fluid was produced separately in mice from each of one of the 6 hybridomas secreting $\alpha_v\beta_3$ complex-specific antibodies and the control M399 hybridoma. The ascites fluid was clarified to remove the lipid and purified on a HiTrap® Protein G column according to the manufacturer's recommendations (Pharmacia Biotech) or a Protein A column (Pharmacia) using the BioRad Protein A MAPS II buffer system. The eluted fractions were dialyzed extensively against PBS and checked for purity by SDS-PAGE. The purified antibodies were >90% pure as determined by Coomassie blue stain and comigrated with an IgG1 K, MOPC-21 (Sigma). The purified antibodies were then assayed in the $\alpha_v\beta$ capture assay to determine if they retained the ability to bind $\alpha_v\beta_3$. All 6 antibodies from fusions P112 and P113 bound $^{125}$I-labeled $\alpha_v\beta_3$ in a dose dependent fashion whereas the control IgGr κ antibody, M399, did not. See FIG. 1.

Immunolocalization of $\alpha_v\beta_3$ in Human Placenta Tissue and Human Colon Carcinoma Tissue Sections of frozen human placenta were treated with 3% $H_2O_2$ for 5 minutes to block endogenous peroxidase activity, washed with PBS and then incubated with 5% BSA in phosphate buffered saline (PBS) and processed for immunohistochemical detection of a fad Formalin-fixed human colon carcinoma tissue was obtained from the Northwestern School of Medicine, Department of Pathology and processed using an automated tissue processor. Samples were embedded in Tissueprep paraffin and cut to 4 micron thick tissue sections using a Reichert-Jung Microtome and dried onto conventional glass slides at 59° C. for 30 minutes. Afterwards, the sections were de-paraffinized with xylene and rehydrated through graded alcohol to distilled water. Rehydrated sections were treated with 3% $H_2O_2$ for 20 minutes, washed with PBS, incubated in PBS containing 2% non-fat dry milk (solution A) for 20 minutes and processed for immunohistochemical detection of $\alpha_v\beta_3$.

Sections of human placenta and human colon carcinoma incubated with anti-$\alpha_v\beta_3$ monoclonal antibody (P112-4C1) diluted in solution A to a concentration of 18 μg/ml or with a commercially-available, isotype-matched irrelevant or control immunoglobulin (Zymed) diluted to 18 μg/ml in solution A. After a 1 hour incubation, sections were washed with PBS and then incubated for 40 minutes with biotinylated horse anti-mouse IgG (Vector Laboratories) diluted 1:100 in PBS containing normal horse serum and then washed with PBS. Bound antibody was detected using a chromogenic avidin-biotin conjugate method VECTASTAIN® (Elite ABC and Vector DAB kit; Vector® Laboratories) according to the manufacturers recommended procedures. Sections were then rinsed in tap water and counter-stained in Lerners #3 hematoxylin for 20 seconds, rinsed in tap water, placed in 0.05% acid alcohol for 4 seconds, rinsed in tap water for 1 minute, incubated in blueing hematoxylin reagent for 30 seconds and then in tap water for 1 minute. Finally, sections were dehydrated in ethanol, cleared with xylene and cover-slipped.

Images of sections of human placenta and human colon carcinoma were captured using a Nikon MICROPHET FXA microscope and a Sony DKC-5000 Digital camera. Sections were scanned to locate the selected field of interest, after which, the images were captured by digital camera and downloaded into a photo design program (Adope Photoshop® 4.0, Adobe Image Systems, Inc.). Scale bars were added to indicate magnification, and the images combined and annotated.

$\alpha_v\beta_3$ and $\alpha_{IIb}\beta_{IIIa}$ Capture Assay 96-well plates (Dynatech, Chantilly, Va.) were coated with 0.5 μg/well goat anti-mouse IgG Fc-specific monoclonal antibody (Sigma, St. Louis, Mo.) in borate buffered saline, pH 8.2 overnight at 4° C. Assay plates were emptied and 200 μl/well of 1% BSA in PBS and 0.05% Tween-20 was added to block unreacted sites in wells. Following a 2 hour incubation at 37° C., the plates were washed 3 times with saline and 0.05% Tween-20 (TS). Sample (mouse sera, hybridoma supernatant or purified monoclonal antibody) was added (50 μl/well) and incubated 90 min at 37° C. The plates were washed 3 times in TS and approximately 100, 000 cpm/well of $^{125}$I-labeled $\alpha_v\beta_3$ or $^{125}$I-labeled $\alpha_{IIb}\beta_{IIIa}$ in Tris-buffered saline containing 1 mM $Ca^{++}$, $Mg^{++}$, and $Mn^{++}$, pH 7.4 and 1% BSA & 50 mM octylglucoside were added and incubated for 2 hours at 37° C. The plates were then washed 3 times with TS and the wells were counted in a gamma counter.

Osteopontin Purification

Full-length human osteopontin cDNA was expressed in E. coli as a 6×His-fusion protein using the QIAEXPRESS PQE expression system as described by the manufacturer (Qiagen, Chatsworth Calif.). Osteopontin was purified by Ni-NTA affinity chromatography according to the manufacturers recommendations (Qiagen) and then further purified by MonoQ (Pharmacia, Piscataway, N.J.) chromatography. Osteopontin was judged greater than 95% pure by SDS gel electrophoresis.

Purification of the Vitronectin Receptor ($\alpha_v\beta_3$)

Human vitronectin receptor ($\alpha_v\beta_3$) and the human platelet receptor ($\alpha_{IIb}\beta_{IIIa}$) was purified from human placenta as previously described (Pytela, R., Pierschbacher, M. D., Argraves, S., Suzuki, S., and Rouslahti, E., *Methods in Enzymology,* Vol. 144 (1987) 475; Yatohgo, T., Izumi, M., Kashiwagi, H., and Hayashi, M., Cell structure and Function, Vol. 13 (1988) 281). $^{125}$I-labeled $\alpha_v\beta_3$ and $^{125}$I-labeled $\alpha_{IIb}\beta_{IIIa}$ were generated by iodinating the unlabeled precursors using Iodogen according to the recommendation of the manufacturer.

M21 Migration Assay

M21 Melanoma cell line was obtained from J. W. Smith (Burnham Institute, La Jolla) and maintained in RPMI 1640 supplemented with 10% FBS, pen-strep (200 U/ml) and L-glut (2 mM). Fibrinogen and vitronectin were purified from human plasma as previously described (Yatohgo et al., *Cell Struct. Func.*, Vol. 13 (1988) 281; Fuller, et al., *Methods in Enzymology* Vol. 163 (1988) 44474).

Extracellular matrix proteins (eg., fibrinogen) were coated on the bottom of Costar transwell membranes at a concentration of 5 $\mu$g/ml. Following a 2 hour coating period at 37° C., the migration assay was initiated by the addition of $2 \times 10^5$ cells to the upper chamber of the reservoir. Migration assays were performed in HBSS, 50 mM HEPES, 1 mg/ml BSA, 0.5 mM $Ca^{2+}$, 0.5 mM $Mg^{2+}$, and 0.2 mM $Mn^{2+}$. Cells were allowed to migrate for 18 hours or 20 hours at 37° C. The upper reservoir was gently swabbed with a cotton-tipped applicator to remove cells from the upper filter surface. The filter was removed and cells on the lower surface were stained with DIFF-QUIK (Baxter). Cells occupying three to five random high power microscopic fields were counted and averaged. For inhibition studies, the inhibitors were incubated with the cells for 30 minutes at 37° C. before addition to the transwell.

M21 Cell Adhesion Assay

Fibrinogen was diluted to 10 $\mu$g/ml in coating buffer (20 mM Tris·HCl, 150 mM NaCl, pH 7.4) and 100 $\mu$l was added to each well of IMMULON2 96-well plates (manufactured by Dynatech, Chantilly, Va.) and incubated overnight at 4° C. The plates were washed (50 mM Tris·HCl, 150 mM NaCl, pH 7.4) and then available protein binding sites blocked by addition of adhesion buffer (1×Hanks Balanced Salt Solution without $Ca^{2+}$ and $Mg^{2+}$ (Sigma), plus 50 mM Hepes, pH 7.4) containing 1% BSA.

M21 cells were washed with HBSS ($Ca^{2+}$ and $Mg^{2+}$ free), incubated in cell dissociation solution (Sigma) for 5 minutes at 37° C. and then washed by centrifugation/resuspension in adhesion buffer containing 200 $\mu$M $Mn^{2+}$.

Cells and various concentrations of mAb were combined in adhesion buffer containing 200 $\mu$M $Mn^{2+}$, added to plates and incubated for 30 minutes at 37° C. The plates were gently washed with 50 nM Tris-HCl, 150 mM NaCl, pH 7.4, and 100 $\mu$L of cell lysis/substrate buffer (50 mM Na acetate, pH 5.0 containing 0.5dsr britob-100 and 0.3 mg/ml of p-nitrophenyl phosphate (Sigma)) was added to each well and incubated for 1 hour at room temperature; 50 $\mu$L of 1N NaOH was added to develop color and the plate absorbance was measured at 412 nm. The number of cells bound/well were determined by reference to a standard curve generated with known numbers of cells.

293 Cell Binding Assay

Human vitronectin was purified from fresh frozen plasma as previously described (Yatohgo, T., Izuini, M., Kashiwagi, H., and Hayashi, M., Cell structure and Function, Vol. 13 (1988) 281). 293 cells were transfected with the $\beta$3 and $\beta$5 integrin subunits as described below.

96-well plates (IMMULON2, Dynatech, Chantilly, Va.) were coated with vitronectin, 50 $\mu$l/well in TS (0 mM Tris, 150 mM NaCl, pH 7.4 (TS), overnight at 4° C. Unreacted sites were blocked with lt BSA in TS, 200 $\mu$l/well for 2 hrs at 37° C. Antibodies were diluted in Hank's Buffered Salt Solution ($Ca^+Mg^+$ free) (HBSS) & 20 mM Hepes & 0.1% BSA & 200 $\mu$M MnCl. 293 cells transfected with $\beta_3$ (293/$\beta_3$), 293 cells transfected with $\beta_5$ (293/$\beta_5$), and untransfected 293 cells (293/$\beta_1$) were removed from flasks with Cell Dissociation Buffer (Sigma, St. Louis, Mo.) and washed 3 times with HBSS. Cells were counted and diluted to $2 \times 10^6$ cells/ml in HBSS & 20 mM Hepes & 0.1% BSA & 200 gM MnCl. Equal volumes of cells were mixed with diluted antibodies and incubated 30 min at 37° C. 100 $\mu$l/well of cell/antibody mixture was then added to vitronectin coated plates and plates were incubated for 30 min at 37° C. Plates were washed 3 times with HBSS to remove unbound cells and 100 $\mu$l of HBSS & 200 $\mu$M MnCl was added per well. The MTT kit (Promega) was used to detect the number of viable attached cells.

Flow Cytometry Methods $2 \times 10^5$ to $5 \times 10^5$ cells were incubated with 1 $\mu$g primary antibody in FACS buffer (1 BSA/PBS+0.1% $NaN_3$) at 4° C. for 30–60 min., washed, then incubated 30–45 min. at 4° C. with a FITC-conjugated goat anti-mouse F(ab')$^2$ secondary antibody (Zymed Laboratories, Inc., San Francisco, Calif.). Cells were washed and resuspended in buffer with propidium iodide (PI), then analyzed by flow cytometry (FACScan™; Becton Dickinson Immunocytometry Systems; San Jose, Calif.). Viable cells were gated on the basis of PI exclusion.

Table 1 shows the binding of anti-integrin monoclonal antibodies to 293/wild type (wt), 293/$\beta_3$ and 293/$\beta_5$ cells using immunofluorescence and flow cytometry. The anti-$\alpha_v\beta_3$ antibodies P113-7D6, P112-4C1, P113-12A6, P112-11D2, P112-10D4, P113-1F3 and LM609, bind to 293 cells transfected with the human $\beta_3$ cDNA (293/$\beta_3$ cells), but not wild type 293 cells (293/wt) or 293 cells transfected with human $\beta_5$ CDNA (293/$\beta_5$). The complex-specific antibody, P1F6 ($\alpha_v\beta_5$; Chemicon), binds only to 293/$\beta$5 cells and P4C10 ($\beta_1$; GIBCO) binds to all three cells lines, consistent with the previous report showing that wild type 293 cells express $\alpha_v\beta_1$, but not $\alpha_v\beta_3$ (Bodary and McLean, *J. Biol. Chem.* Vol. 265 (1990) 5938).

TABLE 1

| Cell line | 293/wt | 293/$\beta$3 | 293/$\beta$5 |
|---|---|---|---|
| P4C10 ($\beta_1$) | ++ | ++ | ++ |
| P1F$_6$ ($\alpha_v\beta_5$) | – | – | ++ |
| LM609 | – | ++ | – |
| P113-7D6 | – | ++ | – |
| P113-1F3 | – | ++ | – |
| P112-10D4 | – | ++ | – |
| P113-12A6 | – | ++ | – |
| P112-4C1 | – | ++ | – |
| P112-11D2 | – | ++ | – |

Table 1 shows $\beta_v\beta_3$ antibody binding to 293/wt, 293/$\beta_3$ and 293/$\beta_5$ cells by immunofluorescence and flow cytometry. Cell staining fluorescence intensity of specific antibodies is reported relative to the control antibody M399: (–) <2-fold; (+/–) 2 to 5- fold; (+) 5 to 10-fold; (++) 10 to 50-fold. The cells lines are designated wild type 293 (293/wt), 293 cells transfected with human $\beta$3 (293/$\beta_3$) and 293 cells transfected with human $\beta$3 (293/$\beta_3$).

293 Cell Engineering 293 cells naturally express $\alpha_v\beta_1$, $\alpha_2\beta_1$, $\alpha_5\beta_1$, and $\alpha_6\beta_1$ with little or no detectable $\alpha_v\beta_3$ (Bodary & McLean, *J. Biol. Chem.*, Vol. 265 (1990) 5938). Cells were transfected using LIPOFECTAMINE according to the manufacturer's recommendations (Gibco BRL, Gaithersburg, Md.) with $\beta_3$ or $\beta_5$ cDNA in the mammalian expression vector PCDNA3 (Invitrogen Corporation) which confers Neomycin resistance (Southern, P. J. And Berg, P., *J. Mol. Appl. Gen.*, Vol. 1 (1982) 327).

Individual clones were generated by limiting dilution and expanded in the presence of antibiotic. High expression levels of $\alpha_v\beta_3$ or $\alpha_v\beta_5$ were confirmed by flow cytometry using the $\alpha_v\beta_3$ complex-specific mAb LM609 (Chemicon, Temecula, Calif.; *Proc. Natl. Acad. Sci. USA*, Vol. 84 (1987) 6471 and the $\alpha_v\beta_5$ complex-specific antibody P1F6 (GIBCO).

Osteoclast Adhesion Assay

Rabbit osteoclasts were obtained from the fore and hind limb bones of 5 day old rabbit pups. Skin and muscle were removed from bones and the bones were pulverized in α MEM containing 20 mM Hepes pH 7.0 and 1% BSA. Clumps of tissue and the released cells were resuspended in α MEM containing 20 mM Hepes pH 7.0 and 1% BSA, clumps of cells were allowed to sediment at unit gravity and the osteoclast containing supernatant was removed and diluted in α MEM & 20 mM Hepes & 1% BSA.

Human osteopontin (OPN) was produced recombinantly as previously described. 96-well plates (IMMULON2 Dynatech, Chantilly, Va.) were coated with 5 μg/ml OPN in 20 mM Tris, 150 mM $NaCl_2$, pH 7.4 (TS) overnight at 4° C. Unreacted sites were blocked with 1% BSA in TS, 200 μl/well) for 2 hours at 37° C. Plates were washed 3 times with TS buffer and 100 μl/well of antibodies diluted in α MEM & 20 mM Hepes & 1% BSA were added. Diluted osteoclasts, 100 μl/well, were added to plates and plates were incubated for 60 min at 37° C. Plates were washed 3 times with α MEM & 1% BSA and 100 μl/well of NPP/ Tartrate Lysis Buffer (50 mM sodium acetate, 0.5% triton X-100, 0.25 mg/ml p-Nitrophenyl phosphate and 6.7 mM tartrate) was added and incubated for 1 hour at 37° C. Finally, 0.1N NaOH (50 μl/well) was added and the absorbance at 405 nM determined. The number of cells bound/ well were determined by reference to a standard curve generated with known numbers of cells.

Endothelial Cell Proliferation Assay

Human dermal microvascular endothelial cells were purchased from Clonetics (San Diego, Calif.) and used for experiments at passages 3–10. Cells were grown in gelatin-coated (1 μmg/ml) flasks and maintained in MCDB 131 (Gibco), 5% FBS (Hyclone) 100 μl/ml mitogen (Biomedical Technologies), 100 μl/ml porcine intestinal heparin (Sigma) 2 mM L-glutamine and 100 U/ml penicillin/ 100 μg/ml streptomycin (Gibco) at 37° C., 5% $CO_2$.

For proliferation experiments, 10 ng/mL human bFGF (R & D Systems) was used in place of mitogen and the final concentration of heparin was reduced to 80 μg/mL. Cells were harvested from flasks by trypsinization and plated at $4-6\times10^3$ cells/well (100 μl/well) onto 96 well microtiter plates precoated with osteopontin (10 μg/ml in Hanks Balanced Salt Solution; 100 μl/well). The cells were incubated for 2 hrs at 37° C. to allow cell attachment and then monoclonal antibodies (at various concentrations) were added directly to the wells. The plates were returned to the incubator and were grown for ~4 days (~80% confluence) with refeeding every other day. On the final day the cells were supplied fresh medium (not containing antibodies) and proliferation was monitored by adding the REDOX indicator Alamar Blue (Biosource International) in an amount equal to 10% of the culture volume. The plates were incubated for an additional 4–5 hrs and fluorescence at 545/575 nm (excitation/emission) was measured using a PANDEX Fluorescence Concentration Analyzer. The final data was expressed as a percentage of inhibition (comparing antibody treated cells to untreated cells).

Other variations and modifications of this invention will be obvious to those skilled in the art. This invention is not limited except as set forth in the claims.

We claim:

1. A complex-specific anti-$\alpha_v\beta_3$ integrin monoclonal antibody selected from the group consisting of P113-7D6 (HB-12224), P112-4C1 (HB-12225), P113-12A6 (HB-12226), P112-11D2 (HB-12227), P112-10D4 (HB12228) or P113-1F3 (HB-12229).

2. A pharmaceutical composition suitable for use in humans comprising the monoclonal antibody of claim 1.

3. A monoclonal antibody that is P113-7D6 (HB-12224).

4. A monoclonal antibody that is P112-4C1 (HB-12225).

5. A monoclonal antibody that is P113-12A6 (HB-12226).

6. A monoclonal antibody that is P112-11D2 (HB-12227).

7. A monoclonal antibody that is P112-10D4 (HB-12228).

8. A monoclonal antibody that is P113-1F3 (HB-12229).

9. A pharmaceutical composition comprising a monoclonal antibody selected from the group consisting of P113-7D6 (HB-12224), P112-4C1 (HB-12225), P113-12A6 (EB-12226), P112-11D2 (HB-12227), P112-10D4 (HB12228) or P113-1F3 (HB-12229) and at least one excipient.

10. A method for treating conditions mediated by $\alpha_v\beta_3$ integrin in a mammal in need of such treatment comprising administering an effective $\alpha_v\beta_3$ integrin inhibiting amount of an antibody of claim 1 wherein the condition is osteoporosis, humoral hypercalcemia of malignancy, mediated by smooth muscle cell migration, atherosclerosis restenosis, ocular neovascularization, macular degeneration, diabetic retinopathy, psoriasis, or rheumatoid arthritis.

11. A method according to claim 10 wherein the condition is osteoporosis.

12. A method according to claim 10 wherein the condition is humoral hypercalcemia of malignancy.

13. A method according to claim 10 wherein the condition is mediated by smooth muscle cell migration.

14. The method of claim 13, wherein the condition is atherosclerosis.

15. A method according to claim 10 wherein the condition is restenosis.

16. A method according to claim 10 wherein the condition is selected from the group consisting of ocular neovascularization, macular degeneration and diabetic retinopathy.

17. A method according to claim 10 wherein the condition is psoriasis.

18. A method according to claim 10 wherein the condition is rheumatoid arthritis.

19. The method of claim 1, wherein $\alpha_v\beta_3$-integrin-bearing cells are killed.

20. The method of claim 1, wherein the growth of $\alpha_v\beta_3$-integrin-bearing cells is inhibited.

21. The method of claim 1, wherein the monoclonal antibody or fragment thereof is conjugated to a cytotoxic or cytostatic agent selected from the group consisting of doxorubicin, daunomycin, methotrexate, cisplatin, bleomycin, vinblastine, mitomycin C, idarubicin, morpholinodoxorubicin, melphalan, cytosine arabinoside, 5-fluorouracil, and neocarzinostatin.

22. A method for delivering a radioisotope to cells having an $\alpha_v\beta_3$-integrin, comprising contacting the cells with a monoclonal antibody of claim 1, or fragment thereof containing the paratope, wherein the antibody or fragment thereof is conjugated to the radioisotope.

23. The method of claim 22 wherein the radioisotope is selected from the group consisting of $^{64}Cu$, $^{67}Cu$, $^{90}Y$, $^{99m}Tc$, $^{103}Pd$, $^{105}Rh$, $^{109}Pd$, $^{111}n$, $^{125}I$, $^{131}I$, $^{153}Sm$, $^{186}Re$, $^{188}Re$, $^{192}Ir$, $^{198}Au$, $^{203}pPb$, $^{212}Pb$, $^{212}Bi$ and 241Am.

24. A method for delivering a bacterial toxin to cells having an $\alpha_v\beta_3$-integrin, comprising contacting the cells with a monoclonal antibody of claim 1, or fragment thereof containing the paratope, wherein the antibody or fragment thereof is conjugated to the bacterial toxin.

25. The method of claim 24 wherein the bacterial toxin is selected from the group consisting of Pseudomonas exotoxin, diphtheria toxin and shiga toxin.

26. A method for delivering a plant toxin to cells having an $\alpha_v\beta_3$-integrin, comprising contacting the cells with a monoclonal antibody of claim 1, or fragment thereof containing the paratope, wherein the antibody or fragment thereof is conjugated to the plant toxin.

27. The method of claim 26 wherein the plant toxin is selected from the group consisting of ricin, abrin, modeccin, gelonin, pokeweed antiviral protein (PAP), $\alpha$-amanitin, ribosome inhibiting protein (RIP), barley RIP, wheat RIP, corn RIP and flax RIP.

28. The hybridoma cell capable of making monoclonal antibody [having the characteristics of monoclonal antibody] P113-7D6 (HB-12224).

29. The hybridoma cell capable of making monoclonal antibody [having the characteristics of monoclonal antibody) P112-4C1 (HB-12225).

30. The hybridoma cell capable of making monoclonal antibody P113-12A6 (HB-12226).

31. The hybridoma cell capable of making monoclonal antibody P112-lD2 (HB-12227).

32. The hybridoma cell capable of making monoclonal antibody P112-10D4 (HB-12228).

33. The hybridoma cell capable of making monoclonal antibody P113-1F3 (HB-12229).

* * * * *